United States Patent
Jolicoeur et al.

(10) Patent No.: US 6,184,436 B1
(45) Date of Patent: Feb. 6, 2001

(54) TRANSGENIC MICE EXPRESSING HIV-1 IN IMMUNE CELLS

(75) Inventors: Paul Jolicoeur, Outremont; Zaher Hanna, Brossard; Denis G. Kay, Ile Perrot, all of (CA)

(73) Assignee: Institut de Recherches Cliniques de Montreal, Montréal (CA)

(*) Notice: Under 35 U.S.C. 154(b), the term of this patent shall be extended for 0 days.

(21) Appl. No.: 09/432,223

(22) Filed: Nov. 3, 1999

Related U.S. Application Data

(63) Continuation of application No. PCT/CA98/00434, filed on May 5, 1998.

(30) Foreign Application Priority Data

May 6, 1997 (CA) .................................................. 2204572

(51) Int. Cl.[7] ......................... A01K 67/00; A01K 67/033; A01K 67/027; G01N 33/00
(52) U.S. Cl. .................................. 800/18; 800/1; 800/3; 800/8; 514/44
(58) Field of Search ................................ 800/18, 8, 3, 1; 514/44, 1

(56) References Cited

U.S. PATENT DOCUMENTS 5,574,206 * 11/1996 Jolicoeur .................................. 800/2

OTHER PUBLICATIONS

Salmon, P. et al. The Journal of Immunology 156(5):1873–1879, Mar. 1996.*
Brady et al., Journal of Virology., 1994, vol. 75 (10), pp. 2549–2558.
Hanna Z et al., Mol. Cell, Biol., 1994, vol. 14, pp. 1084–1094.
Lindemann D et al., J. of Experimental Medicine, 1994, vol. 179, pp. 797–807.
Skowronski, J et al., Embo J., 1993, vol. 12, pp. 703–713.
Brady, H.J. et al., Embo J., 1993, vol. 12, pp. 4923–4932.
Hanna, Z et al., J. Virol., 1998, vol. 72, pp. 121–132.
Jolicoeur et al., J. of Molecular Medicine, 1997, vol. 75 (7), p. b177.
Klotman PE et al., AIDS, 1995, 9:313–324.
Leonard JM et al., Science, 1988, 242:1665–1670.
Schnittman SM et al., Science, 1989, 245:305–308.
Scott GB et al., New England J. of Medicine, 1989, 321:1791–1796.
Coodley GO et al., J. of Acquired Immune Deficiency Syndromes, 1994, 7:681–694.
Santoro TJ et al., Virology, 1994, 201:147–151.
Joshi V, Pediatric Hematology & Oncology, 1994, 11:351–355.
Strauss J et al., New England J. of Medicine, 1989, 321:625–630.
Goudreau G et al., Nature Medicine, 1996, 2:655–661.

* cited by examiner

Primary Examiner—Scott D. Priebe
Assistant Examiner—Joseph T. Woitach
(74) Attorney, Agent, or Firm—Shabey Ogilvy Renault; France Côté

(57) ABSTRACT

The present invention relates to a transgenic mouse to serve as a small animal model of AIDS which comprises at least a DNA sequence coding for HIV-1 nef or a HIV-1 DNA genome essentially consisting in entire HIV-1 coding sequences under the control of the human CD4 gene promoter flanked by the enhancer of the mouse CD4 gene for expression in T cells and in cells of monocyte/microphage lineage. There is also provided a method to screen for therapeutic agents for the treatment of AIDS, which comprises the steps of: a) administering the therapeutic agent to the mouse of the present invention; and b) determining the effects of the therapeutic agent.

15 Claims, 15 Drawing Sheets

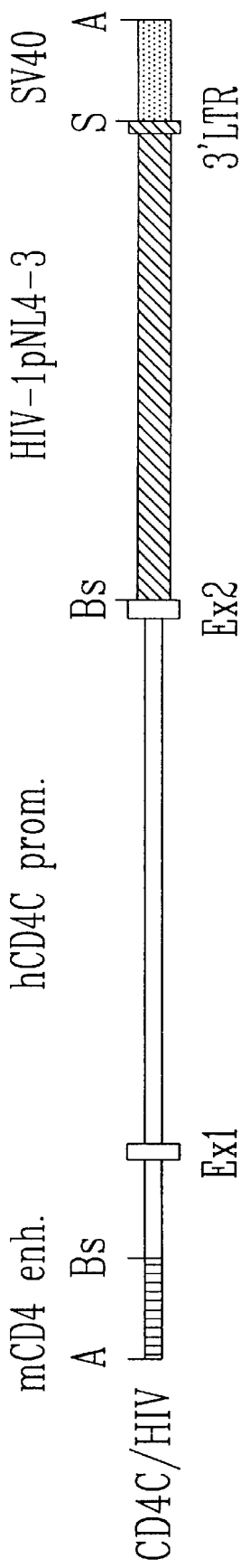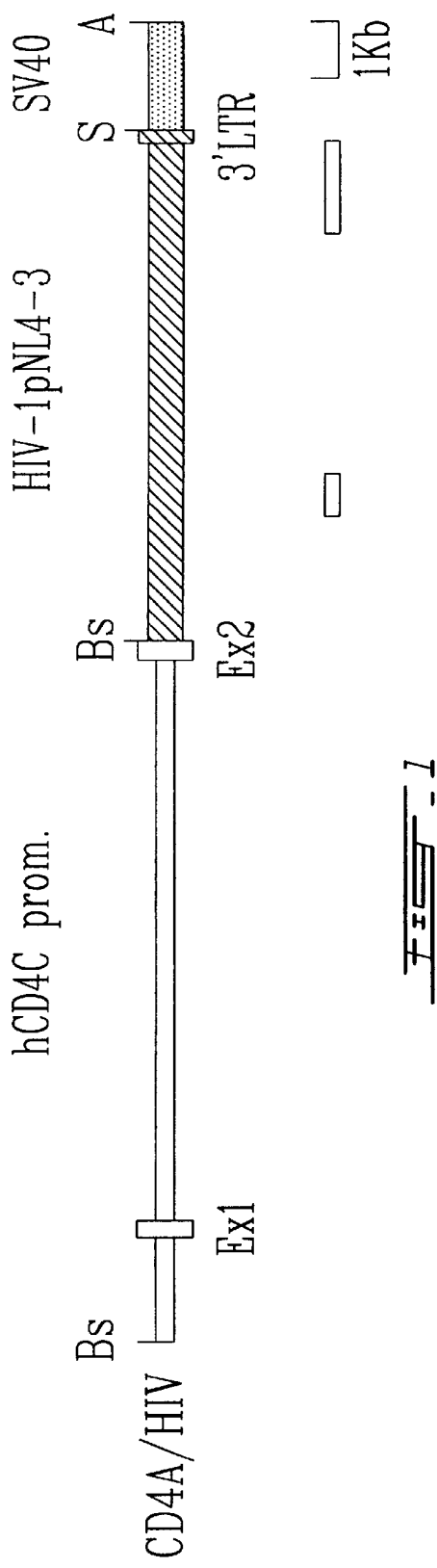
FIG. 1

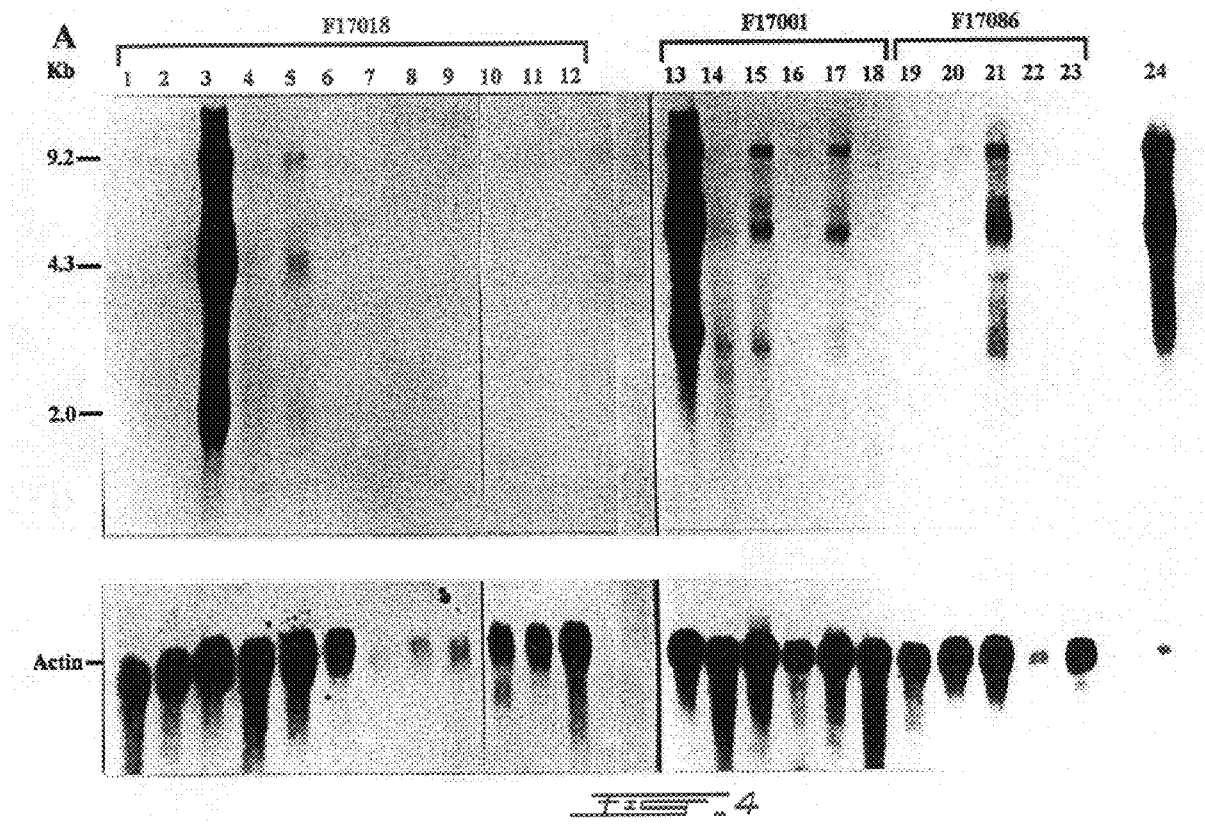

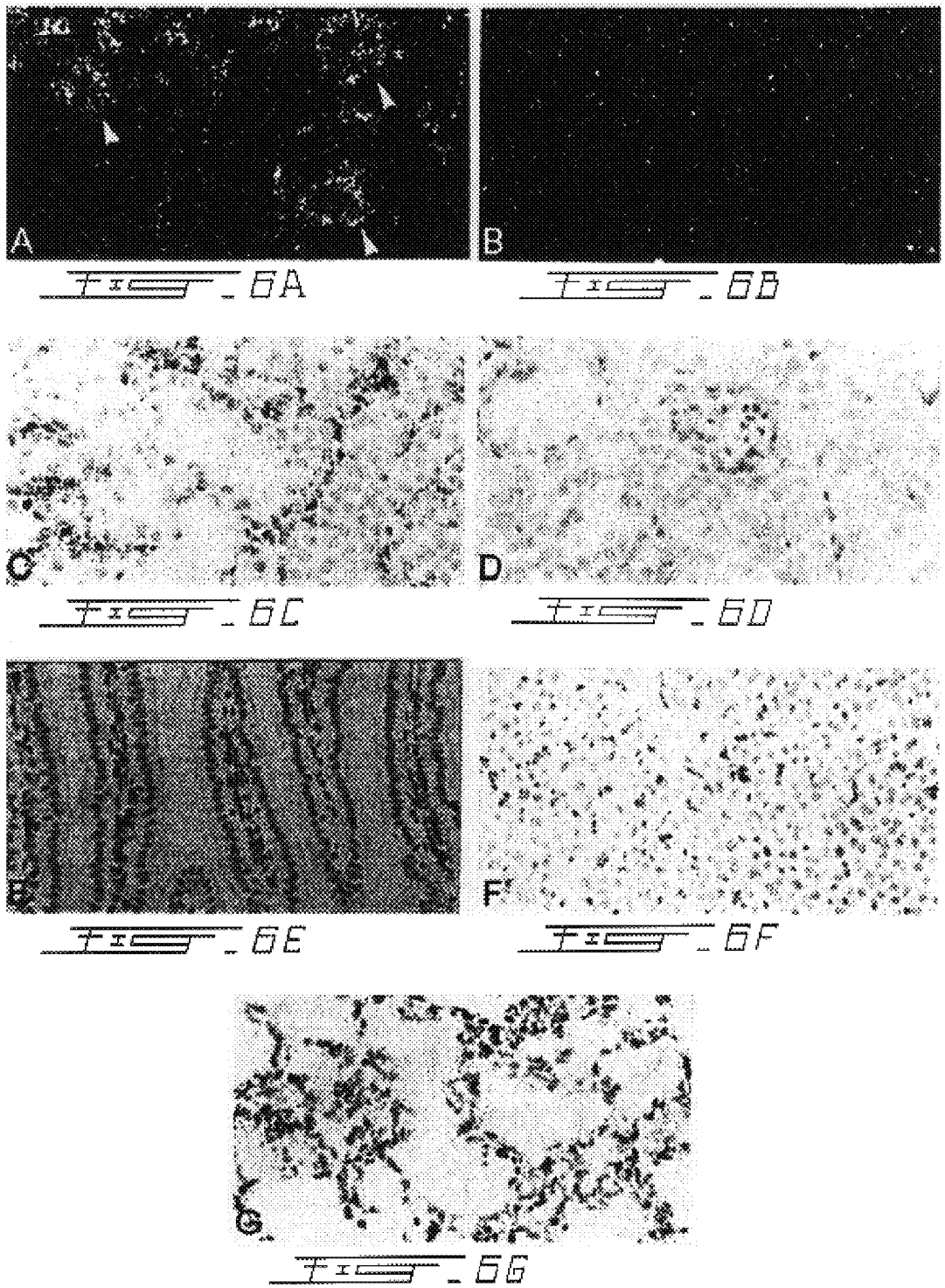

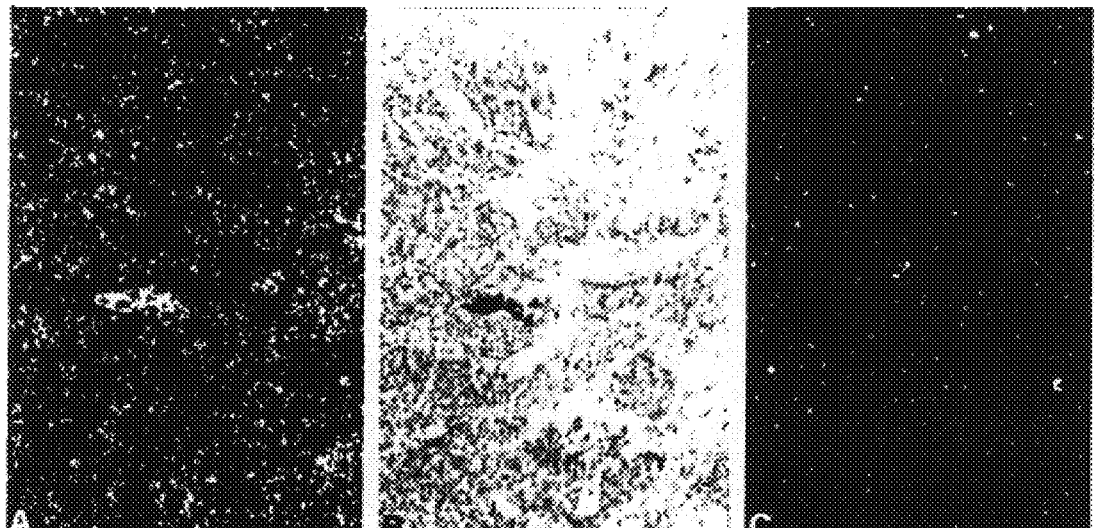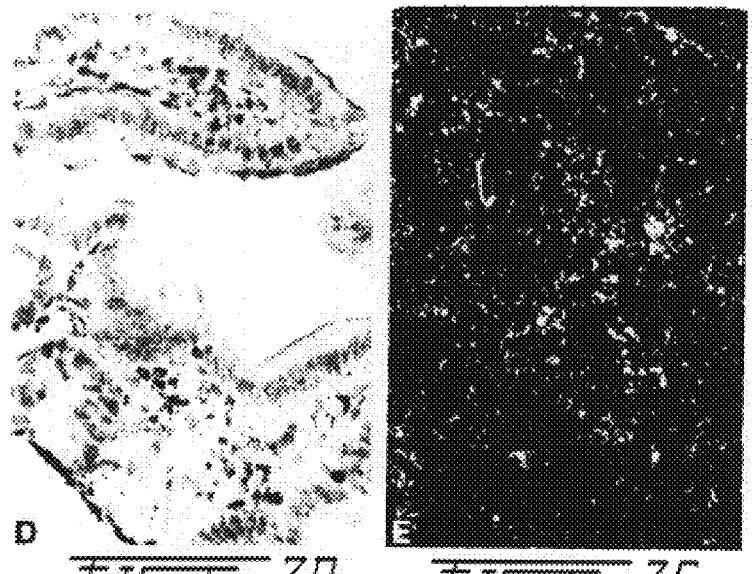

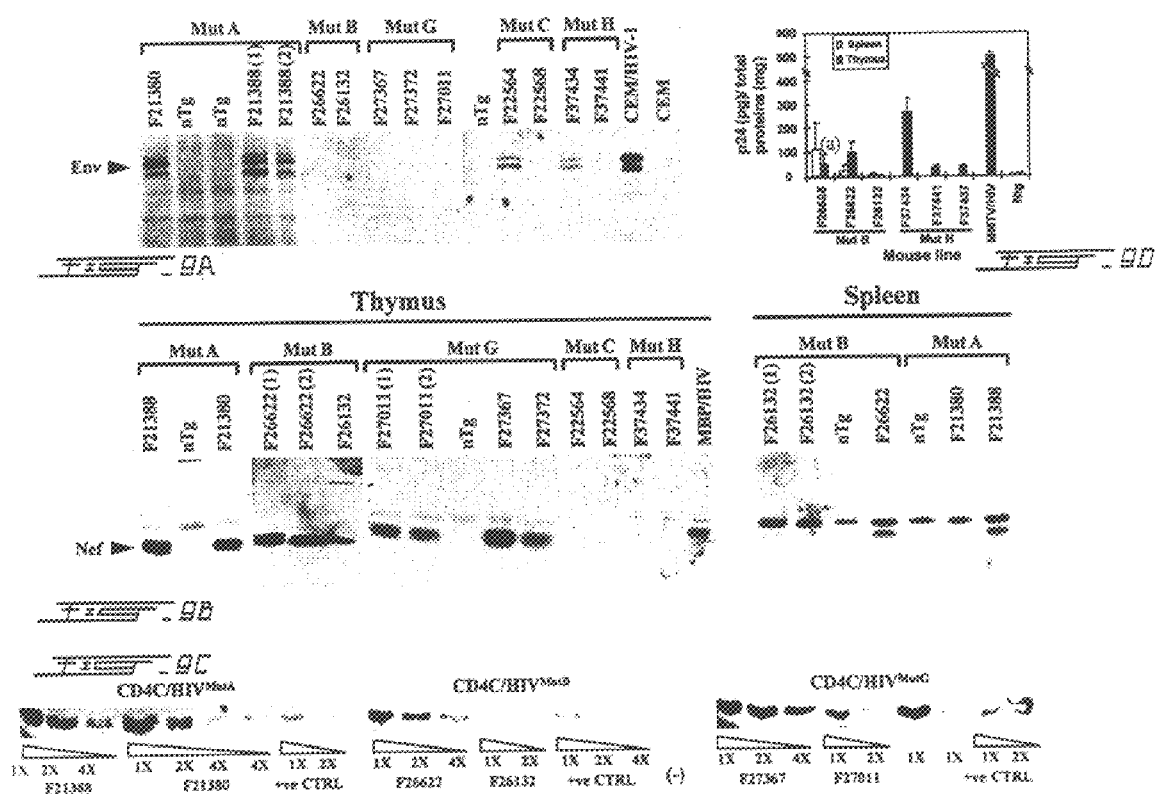

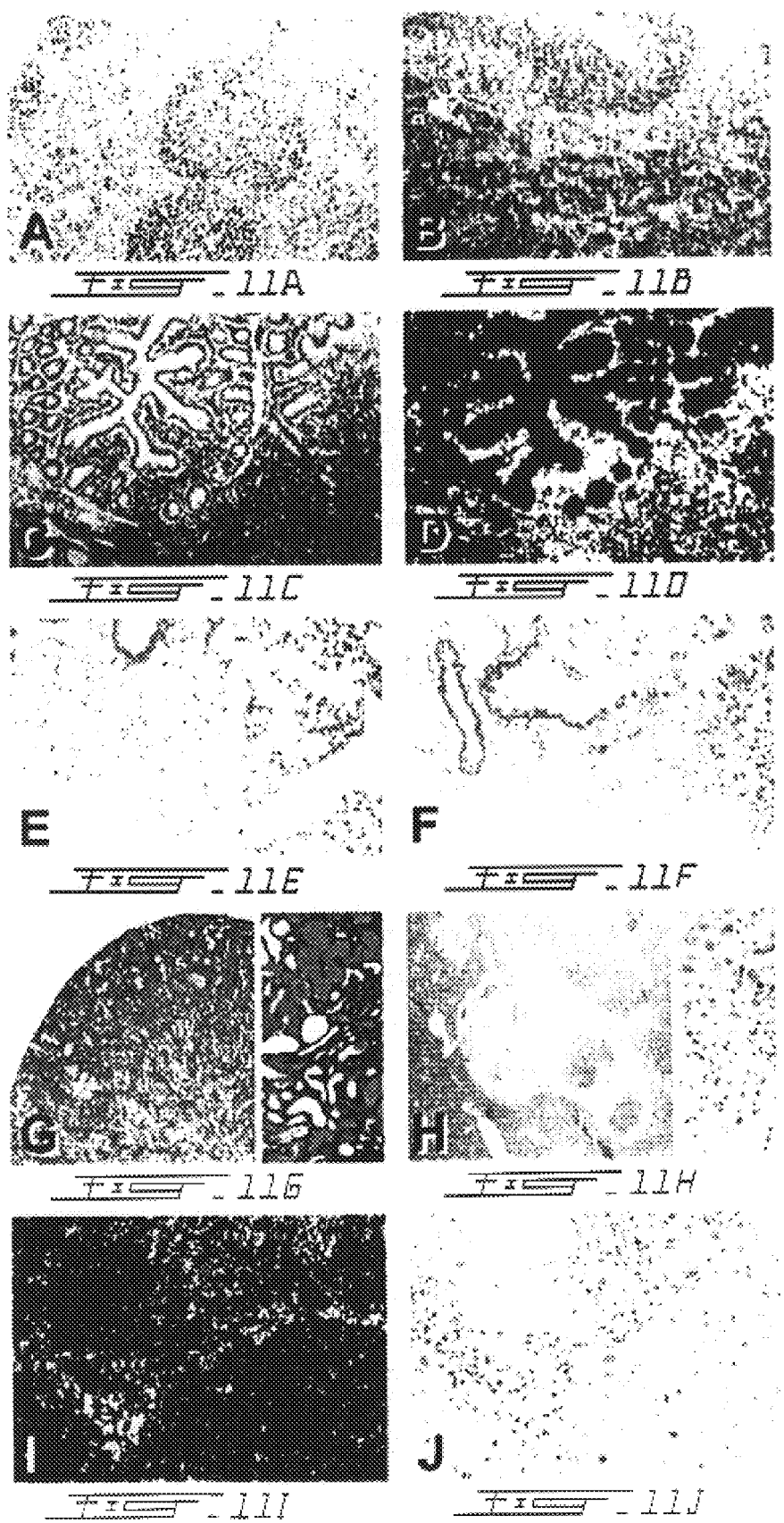

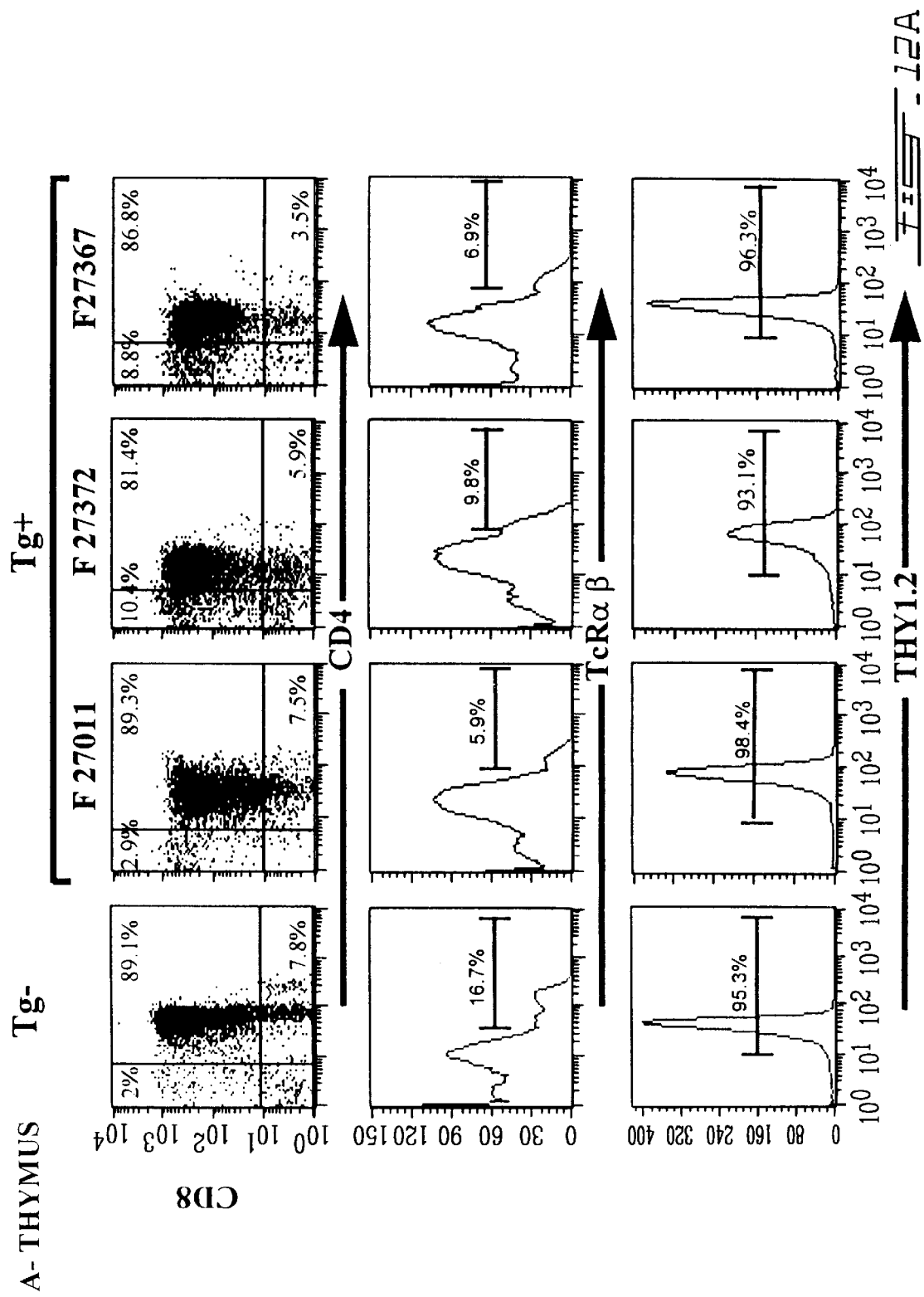

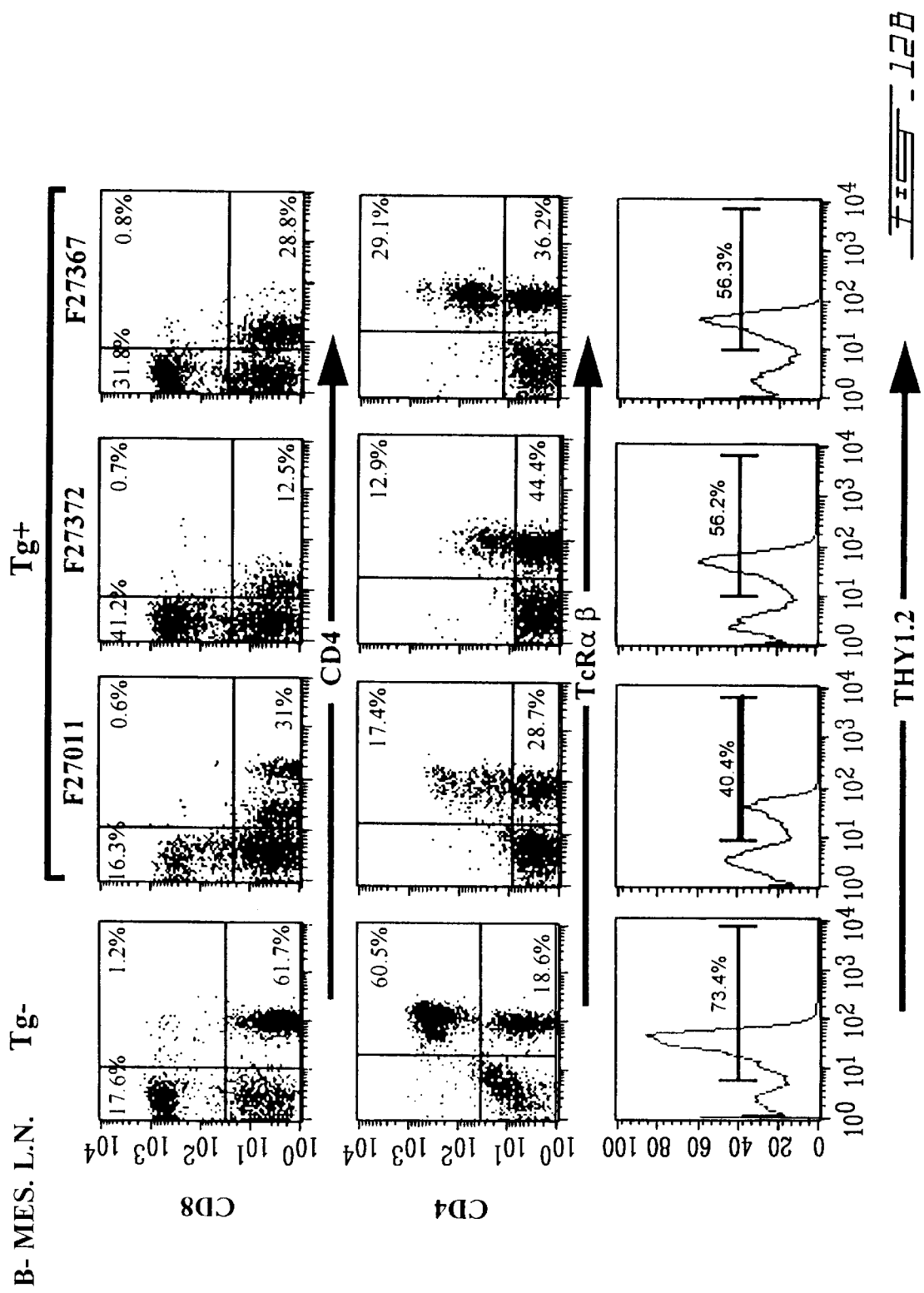

TRANSGENIC MICE EXPRESSING HIV-1 IN IMMUNE CELLS

This application is a continuation of PCT/CA98/00434 filed May 5, 1998 designating the United States and claiming priority of Canadian Patent Application Serial Number 2,204,572 filed May 6, 1997.

BACKGROUND OF THE INVENTION (a) Field of the Invention

The invention relates to a transgenic (Tg) mice expressing at least HIV-1 nef or the entire HIV-1 coding sequences under the control of the human CD4 gene promoter flanked by the enhancer of the mouse CD4 gene to serve as a small animal model of AIDS.

(b) Description of Prior Art

The human immunodeficiency virus type 1 (HIV-1) is the etiologic agent of AIDS. Although the biology of HIV-1 has been intensively studied, the pathogenic mechanisms by which the depletion of $CD4^+$ T lymphocytes occurs and how the severe immune disease characteristic of advanced AIDS is induced are not completely understood. A major obstacle in studying the pathogenesis of HIV-1 infection in vivo and the development of effective vaccines has been the lack of suitable animal models. A small, readily available animal model that could duplicate, in whole or in part, the pathological changes observed in AIDS patients would be a great asset for AIDS research.

Cell tropism for infection by HIV-1 is largely determined by the cell-surface expression of the CD4 antigen and the newly discovered co-receptors (CXCR4/fusin, CCR5). Immature T-cell precursors and mature $CD4^+$ T cells and cells of the dendritic/macrophage lineage (monocytes, dendritic cells, Langerhans cells, macrophages and microglial cells) are those subsets of cells mainly targeted by HIV-1 infection. Ideally, an animal model for HIV-1 infection and AIDS should have the same subsets of cells infectable by or expressing HIV-1. To date, no animal model has been generated that fulfills all these criteria. The best model currently used still remains SAIDS, an AIDS-like syndrome induced in primates by SIV, a simian lentivirus having a structure very similar to that of HIV-1. However, this model is not widely available to all scientists and a virus different from HIV-1 is used for infection. Severe combined immunodeficient (SCID) mice reconstituted with human lymphoid cells have also been used for infection with HIV-1. This biological system offers the advantage of active HIV-1 replication in small animals with a severe depletion of the engrafted $CD4^+$ T cells. However, these mice are relatively difficult to generate and other important manifestations of AIDS are not observed. The third type of models for HIV-1-induced disease currently available are transgenic (Tg) mice expressing all or some HIV-1 gene products. Although the initial interaction of HIV-1 with its cellular receptors and the early replication steps and reinfection cycles are bypassed and cannot be studied in these Tg models, they nevertheless allow investigation of post-integration events in the virus life cycle, such as HIV-1 protein-mediated cytopathic effects and the subsequent host responses.

Several HIV-1 Tg animal models have been developed (Klotman PE et al., AIDS, 1995, 9:313–324). The use of the HIV-1 LTR to express the whole HIV-1 genome in Tg mice led to the development of an AIDS-like syndrome, but this phenotype was observed in a single line (no 13) of Tg mice (Leonard J M et al., Science, 1988, 242:1665–1670). LTR-dependent expression of the 3' half of the HIV-1 genome in Tg mice induced a severe nephropathy. The HIV-1 LTR-driven expression of either nef or tat in Tg mice was found to induce epidermal hyperplasia, while expression of gag or protease in lens fiber cells appears to be responsible for the development of cataracts. Attempts to express HIV-1 nef more specifically in lymphoid cells of Tg mice were made by using the T-cell specific CD3 δ promoter/enhancer element, the TCRβ chain-enhancer promoter element or the CD2 regulatory elements. These Tg animals showed varying degrees of depletion of $CD4^+$ thymocytes and of peripheral T cells, depending on the promoter used. However, additional important characteristics of AIDS were not observed in these mice while other features, such as a large increase of the B cell population, not seen in human AIDS, was observed (Lindemann D et al., J. of Experimental Medicine, 1994, 179:797–807).

It would be highly desirable to be provided with a small animal model of AIDS such as a transgenic mice which would develop a severe AIDS-like disease which would dependent on the levels of HIV-1 expression.

SUMMARY OF THE INVENTION

One aim of the present invention is to provide a small animal model of AIDS such as a transgenic mice which would develop a severe AIDS-like disease which would dependent on the levels of HIV-1 expression.

In an attempt to develop more relevant model of HIV-1 infection, it was an aim of the present invention to express HIV-1 gene products in the same cells of Tg mice as those usually found infected in HIV-1 positive individuals, i.e. CD4 $T^+$ cells and cells of the dendritic/macrophage lineage. The human CD4 gene promoter sequences flanked by the enhancer of the mouse CD4 gene were used to express the whole HIV-1 coding sequences in Tg mice. These Tg mice should represent a model of a relatively high steady-state viral RNA load since all relevant cell subsets should express the transgene in Tg mice. In accordance with the present invention, evidence is presented here that indeed these Tg mice develop a severe AIDS-like disease which is dependent on the levels of HIV-1 expression.

In accordance with the present invention there is provided a transgenic mouse to serve as a small animal model of AIDS which comprises a HIV-1 DNA sequence coding for at least nef under the control of the human CD4 gene promoter flanked by the enhancer of the mouse CD4 gene for expression in T cells and in cells of monocyte/microphage lineage.

In accordance with the present invention there is provided a transgenic mouse to serve as a small animal model of AIDS which comprises a HIV-1 DNA genome essentially consisting in entire HIV-1 coding sequences under the control of the human CD4 gene promoter flanked by the enhancer of the mouse CD4 gene for expression in T cells and in cells of monocyte/microphage lineage.

In accordance with the present invention there is provided a transgenic mouse to serve as a small animal model of AIDS in which the germ cells and somatic cells carry at least one copy of a single transgene that comprises:

a) a HIV-1 DNA sequence coding for at least nef; and
b) a human CD4 gene promoter operatively linked to the HIV-1 DNA genome, wherein the promoter is flanked by the enhancer of the mouse CD4 gene for expression in T cells and in cells of monocyte/microphage lineage;

wherein the transgene is introduced into the mouse or an ancestor thereof as a single transgene.

In accordance with the present invention there is provided a transgenic mouse to serve as a small animal model of AIDS in which the germ cells and somatic cells carry at least one copy of a single transgene that comprises:

a) a HIV-1 DNA genome essentially consisting in entire HIV-1 coding sequences; and b) a human CD4 gene promoter operatively linked to the HIV-1 DNA genome, wherein the promoter is flanked by the enhancer of the mouse CD4 gene for expression in T cells and in cells of monocyte/microphage lineage;

wherein the transgene is introduced into the mouse or an ancestor thereof as a single transgene.

The preferred transgenic mouse of the present invention has the human CD4 gene promoter linked at the is 3' end of the HIV-1 DNA genome.

In accordance with the present invention there is provided a method to screen for therapeutic agents for the treatment of AIDS, which comprises the steps of: a) administering the therapeutic agent to the mouse of the present invention; and b) determining the effects of the therapeutic agent.

In accordance with the present invention there is provided a method for producing a transgenic mouse to serve as a small animal model of AIDS, which comprises the steps of:

a) transferring a transgene into a mouse fertilized oocyte, which transgene comprises:

i) a HIV-1 DNA sequence coding for at least nef or the entire HIV-1 genome; and ii) a human CD4 gene promoter operatively linked to the HIV-1 DNA sequence, wherein the promoter is flanked by the enhancer of the mouse CD4 gene for expression in T cells and in cells of monocyte/microphage lineage;

b) transferring a fertilized oocyte containing the transgene to the uterus of a female mouse;

c) maintaining the mouse of step b) such that the mouse becomes pregnant with an embryo derived from the fertilized oocyte, whereion the embryo develops into a viably born transgenic mouse.

BRIEF DESCRIPTION OF THE DRAWINGS

FIG. 1 illustrates the structure of CD4A/HIV and CD4C/HIV transgenes.

FIG. 4 illustrates the expression specificity of CD4C/HIV transgene in different tissues.

FIG. 6 illustrates the transgene expression assessed by in situ hybridization in extra-lymphoid tissues of CD4C/HIV tg mice. Panel A is a dark field image of the kidney from a Tg animal exhibiting extensive pathology (arrows note transgene expression in the glomeruli as well as ductal regions). Panel B is the same tissue as in panel A hybridized with the transgene sense probe as a control. Panel C and D are bright field images of interstitial infiltrating cells (panel C) and glomerular cells (panel D). Panel E-G are examples of transgene expression in cells of lymphoid morphology in the lamina propria of the intestine (panel E), in liver Kupffer cells (panel F) and in interstitial infiltrating cells and alveolar macrophages (panel G).

FIG. 7 illustrates the RANTES expression assessed by in situ hybridization in CD4C/HIV tg mice. Panels A–C are lymphnode sections illustrating the expression of the chemokine RANTES; panel A is a dark field image and panel B is the light field image of a section hybridized with an antisense probe, and panel C is the same region hybridized with a sense probe as a control. Panels D–E illustrate the RANTES expression in non-lymphnode tissues; cells of the lamina propria of the intestine (panel D), interstitial cells of the kidney (panel E).

FIGS. 9A–D illustrate the expression HIV-1 proteins in CD4C/HIV$^{Mut}$ Tg mice.

FIG. 11 illustrates the pathology and HIV-1 transgene expression in CD4C/HIV$^{Mut}$ Tg mice. Panel A–J represents histological examination and in situ hybridization of various tissue samples; the thymus (panel A and B), the lymph nodes of the intestine (panel C and D), the intra-alveolar exudate (panel E and F), necrotizing granulomas (panel G and H) and the kidney (panel I and J).

FIG. 12 illustrates the flow cytofluorometric analysis of T-cell subsets from CD4C/HIV$^{MutG}$ Tg mice. Panel A represents FACS analysis of non-Tg and Tg cells isolated from the thymus. Panel B represents FACS analysis of non-Tg and Tg peripheral lymphoid cells.

DETAILED DESCRIPTION OF THE INVENTION

Figure 2A:
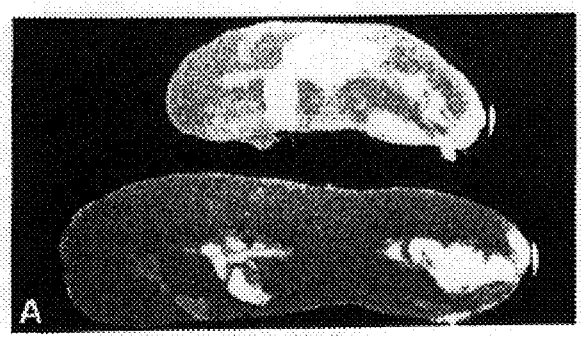
FIG. 2 illustrates the pathology observed in lymphoid tissues from CD4C/HIV Tg mice, comparison with age matched non-Tg control animals. Panel A is a macroscopic view of spleens from non-Tg (bottom) and Tg (top) animals. Panel B is the non-Tg and panel C is the Tg spleen, illustrating the hypocellularity in the Tg spleen. Panel D is the non-Tg and panel E is the Tg thymus, illustrating the disorganization, small size and hypocellularity in the Tg spleen. Panel F is the non-Tg and panel G is the Tg lymph nodes, illustrating the general loss of architecture and hypocellularity of the Tg organ.
Figure 2B:
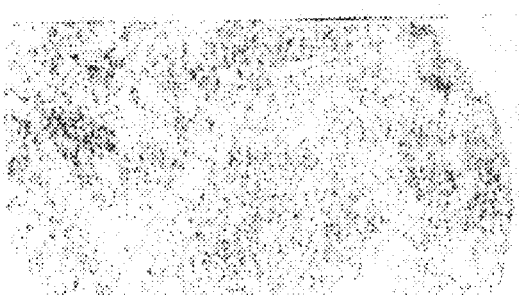

In accordance with the present invention, there is provided a transgenic (Tg) mice expressing the entire HIV-1 coding sequences under the control of the human CD4 gene promoter flanked by the enhancer of the mouse CD4 gene to serve as a small animal model of AIDS.

The transgenic mice of the present invention develop a severe AIDS-like disease leading to early death (<1 month). At autopsy, severe muscle wasting and pathological abnormalities of several organs were apparent. All the lymphoid organs were atrophic and showed loss of architecture, hypocellularity, and in some cases, fibrosis. FACS analysis revealed that $CD4^+CD8^+$ and $CD4^+CD8^-$ thymic T cells were severely depleted while $CD4^-CD8^+$ and $CD4^-CD8^-$ T cells constituted the largest populations of the thymus. Peripheral $CD4^+$ and $CD8^+$ T cells were also severely depleted. The kidneys were small, pale and showed a tubulointerstitial nephritis with tubular atrophy and interstitial fibrosis. Several mice with the severe kidney disease developed edema. The lungs were abnormal, exhibiting a lymphoid interstitial pneumonitis. In addition the expression of RANTES was increased in various tissues of Tg mice relative to the normal controls. Chimeric mice, generated by inoculation of ES cells transfected with the same CD4C/HIV transgene, developed the same disease when sufficient cells of ES cell origin expressed the transgene. Together these results indicate that a certain level of expression of HIV-1 in specific subsets of cells of Tg mice is highly pathogenic. These cell populations are those normally targeted by HIV-1 infection in humans. The numerous pathologies observed in these mice are remarkably similar to those observed in human AIDS and more specifically in paediatric AIDS.

Since all HIV-1 genes were expressed in these mice, we were unable to map the determinant of pathogenicity on (a) specific HIV-1 gene(s). To determine the contribution of individual HIV-1 genes in the pathogenesis of the AIDS-like disease developing in these $CD4C/HIV^{wt}$ Tg mice, we mutated selected HIV-1 genes and constructed five mutant CD4C/HIV DNAs which were assayed in 18 lines of Tg mice. These studies revealed that nef was necessary and sufficient for the induction of the severe AIDS-like disease in these Tg mice.

RNA Purification and Northern Blot Analysis

RNA was isolated by the method of Chomezynski and Sacchi from different tissues and 10 µg from each sample were electrophoresed on formaldehyde agarose gels and processed for hybridization with a $^{32}$P-labeled 8.8 kbp BssHII-SacI HIV-1 probe, as previously described (Goudreau G et al., Nature Medicine, 1996, 2:655–661).

Detection of HIV-1 Proteins

Detection of HIV-1 proteins by Western immunoblotting was performed as previously described (Goudreau G et al., Nature Medicine, 1996, 2:655–661). Polyclonal goat antibodies to gp160 (ERC-188) (1:5000) were obtained through the AIDS Research and Reference Reagent Program, National Institutes of Health. Polyclonal rabbit antibodies against Nef were obtained from V. Erfle (1:1000). Horseradish peroxidase-conjugated secondary antibodies (goat or rabbit) were used at 1:6000 dilution. Proteins were detected using an enhanced chemiluminescent substrate (Amersham). The amount of protein in each lysate was quantitated using a Micro BCA assay (Sigma). HIV-1 p24 gag proteins were quantified by using the Abbott HIVAG-1 Monoclonal ELISA kit, as previously described (Goudreau G et al., Nature Medicine, 1996, 2:655–661).

Flow Cytometry

Cell suspensions were prepared from lymphoid organs and stained with antibodies, (Cederlane Laboratories) as previously described (Hanna Z et al., Mol. Cell. Biol., 1994, 14:1084–1094). Fluorescein-isothiocyanate (FITC)-coupled anti-mouse CD4, phycoerythrin (PE)-coupled anti-mouse CD8 and FITC-coupled anti-mouse TcRαβ antibodies were used. Cytometric analyses were performed using FACscan (Becton Dickinson) as described previously (Hanna Z et al., Mol. Cell. Biol., 1994, 14:1084–1094).

Peritoneal Macrophage Preparation

Mice were injected intraperitoneally with 1 ml of mineral oil 2 days prior to sacrifice. Peritoneal cells were harvested and plated on Petri dishes. The attached macrophages were washed and processed for in situ hybridization (ISH) or collected for RNA extraction.

Microscopic Analysis

Mice were anaesthetized with Avertin™, serum was collected and the animals were exsanguinated with PBS. Lymphoid organs were collected and immersion-fixed in periodate-polylysine-paraformaldehyde fixative (PLP). The remainder of the animal was then perfusion-fixed with PLP fixative. Organs to be assessed were embedded in paraffin, sectioned at 5 µM and stained with hematoxylin and eosin. Tg and control non-Tg tissues were assessed blindly by two investigators (S. J. and D. G. K.)

Measurement of Immunoglobulin (Ig) Levels by ELISA:

ELISA for detection of total serum Ig levels were performed, as previously described (Hanna, Z et al., J. Virol., 1998, 72:121–132).

Proliferation Assays:

Cell proliferation assays were performed on spleen and mesenteric LN cells from Tg and non-Tg littermate controls as previously described (Huang, M. et al., J. Virol., 1991, 65:6562–6571).

In Situ Hybridization

In situ hybridization (ISH) was performed on paraffin-embedded tissues, using $^{35}$S-UTP labeled antisense and control sense RNA probes as described previously (Goudreau G et al., Nature Medicine, 1996, 2:655–661). A mixture of two probes were used: the 1.4 kbp HindIII-SacI (nt 8131 to 9566) of pNL4-3 clone Genebank accession number: M19921) and the 627 bp HindIII fragment (nt 407 to 1034) of the HIV-1 BH102 clone (Genebank accession number: M15654). Tissues from non-Tg control animals hybridized with antisense probes, as well as Tg animal tissues hybridized with sense probes failed to exhibit any specific hybridization signal. RANTES expression was detected using a 373 bp murine cDNA probe cloned by RT-PCR from thymus RNA, with the sense primer 5'-CTCTGCCGCGGGTACCATGAAG and the antisense primer 5'-GTGGCATCCCCAAGCTGGCTAG.

I) Entire HIV-1 Genome

Generation of Tg Mice

The CD4A (12.5 kbp) and CD4C (14.4 kbp) promoters have previously been described (Hanna Z et al., Mol. Cell. Biol., 1994, 14:1084–1094). Each was fused to a 8.8 kpb BssHII-SacI fragment of the HIV-1 pNL4-3 clone and to SV40 polyadenylation sequences as described before (Goudreau G et al., Nature Medicine, 1996, 2:655–661) and cloned in the pBR322 vector to generate CD4A/HIV and CD4C/HIV transgenes, respectively. The transgene DNAs were excised with AatII, purified by agarose gel electrophoresis, and microinjected into fertilized (C57BL/6×C3H)F2 oocytes, as described before (Goudreau G et al., Nature Medicine, 1996, 2:655–661). Mice were bred as heterozygotes with C3H or CD1 mice obtained from Charles River Canada (St. Constant, Quebec, Canada) The presence of the transgene was confirmed by Southern blot hybridization of tail DNA with $^{32}$P-labeled total HIV-1 sequences as a probe, as described previously (Goudreau G et al., Nature Medicine, 1996, 2:655–661). The Tg mice and their non-Tg littermates were housed in the same cages.

Construction of Transgenic (Tg) Mice

The entire HIV-1 coding sequences of the pNL4-3 clone fused to SV40 polyadenylation signal sequences and under the control of the CD4C promoter were used to generate the CD4C/HIV transgene. The CD4C sequences contain the promoter of the human CD4 gene (including exon 1, part of exon 2 and intron 1) with the enhancer of the mouse CD4 gene fused at its 5' end (FIG. 1). The CD4A/HIV DNA contains 12.5 kbp of the human CD4 promoter (white bar and boxes), fused to the HIV-1 pNL4-3 DNA fragment (hatched bar and box) and SV40 polyadenylation sequences (dotted box). The CD4C/HIV construct contains the entire CD4A/HIV construct fused to 1.9 kbp enhancer fragment of the mouse CD4 gene (stippled bar). The HIV-1 fragments cloned in GEM-4 (Promega) and used for riboprobes are illustrated (lower white bars). Restriction sites: A, AatII; Bs, BssHII, S, SacI (FIG. 1).

It was previously shown that these CD4 enhancer/promoter sequences can direct gene expression specifically in the same subsets of cells as those expressing CD4 in humans, i.e. CD4$^+$ T-cells and macrophages (Hanna Z et al., Mol. Cell. Biol., 1994, 14:1084–1094). To avoid the production of infectious HIV-1 particles in cells expressing the transgene, the 5' LTR, part of the 5' untranslated leader sequences and part of 3' LTR of the HIV-1 genome were deleted in the transgene. Another transgene (CD4A/HIV) was constructed by deleting the mouse CD4 enhancer from the CD4C/HIV construct (FIG. 1). Previous studies with the CD4A promoter linked to a reporter gene have revealed that this promoter was much less potent in driving expression of the gene in T cells (Hanna Z et al., Mol. Cell. Biol., 1994, 14:1084–1094). To generate transgenic mice, these two transgene DNAs were separated from vector sequences and then microinjected into (C57BL/6×C3H)F2 one-cell embryos. Five CD4C/HIV (F15564, F17001, F17018, F17027, F17086) and four CD4A/HIV (F21093, F22194, F22200, F22410) founders were produced. Southern blot analysis indicated that the structure of both transgenes appeared grossly intact.

Transmission of the Transgene: Mosaicism of Founder Mice

Founder mice were bred to normal C3H or occasionally on CD-1 mice and tail DNAs from the resulting progeny were analyzed for the presence of the transgene. All founder animals produced litters consisting on average of 7 or more pups. However, the frequency of Tg animals in these litters was significantly lower than expected, except for one founder (F17018), suggesting that these founders were mosaic.

The CD4C/HIV founder F17027 produced only non-Tg pups and non-Tg 12- to 19-day old fetuses, confirming that this founder was indeed mosaic. The CD4C/HIV F17018 male founder died suddenly 3.5 months after birth and no further analysis were carried out due to autolysis. The CD4C/HIV F17086 female founder became ill five months after birth. Autopsy on this animal revealed that it was suffering from intestinal obstruction caused by a large lymphoma. The other three CD4C/HIV founders and the four CD4A/HIV founders appeared healthy during a 12-month period of observation in terms of development, growth, body weight and fertility.

Tg lines could be established from the four CD4A/HIV transgenic founders. However, no Tg lines could be established from the CD4C/HIV founders, since the first generation (N1) of Tg pups either died early or were sacrificed before attaining sexual maturity due to the development of severe disease.

Clinical Phenotype and Pathological Assessment of CD4A/HIV Tg Mice

The CD4A/HIV mice were observed for a period up to 24 months. No clinical phenotype was observed in any of the 76 animals observed. Gross pathological abnormalities in animals sacrificed at 12–14 months were seen in only one animal which exhibited an enlarged spleen (~3×), slightly enlarged lymph nodes and a lung tumor. Histological examination was also negative in these mice. The low expression of the transgene in these mice (see below) may explain the absence of obvious phenotypes or signs of disease.

Clinical Phenotype of CD4C/HIV Tg Mice

Tg mice and non-Tg littermate controls born from the different CD4C/HIV founders were further evaluated. The time course of disease development was similar in all three lines. Over the first two weeks of life, no clinical abnormalities could be detected in the Tg mice, as compared to non-Tg controls. In the third week, the Tg mice were readily distinguishable from their non-Tg littermates by their lower body weight [Tg 7.4±0.8 g (n=8); non-Tg 12.4±2.1 g (n=4)], slow movements and hypoactivity. At later stages, the diseased animals had developed ruffled hair, weakness and had severe tremors and feeding problems. Some of them also had diarrhea (Table 1). These signs developed over a period of a few days before the animals died or before they were sacrificed (between 21–31 days). All affected animals (n=25) from four different founders showed the same phenotype. Only one N1 male mouse (#17950 from founder 17018) lived longer (7 weeks) and reached sexual maturity, but was unable to breed due to its severe illness. Attempts to save the line through in vitro fertilization with the sperm of this older Tg mouse produced two litters. N2 Tg mice (n=2) from these litters also died with the same phenotype (at 25 days). None of the control non-Tg littermates (n=127) kept in the same cages as the Tg mice exhibited a similar phenotype nor detectable abnormalities, indicating that this phenotype was transgene-specific.

TABLE 1

Incidence of disease in CD4C/HIV Tg mice

| | Mice Studied[b] | | | | | | | | | |
|---|---|---|---|---|---|---|---|---|---|---|
| | 15564 | | 17001 | | 17018 | | 17086 | | Total[e] | |
| Pathology observed[a] | + | −[d] | + | −[d] | + | −[d] | + | −[d] | + | −[d] |
| Macroscopic | | | | | | | | | | |
| Time (days) of death[c] | 15 ± 1.7 | | 30.3 ± 05 | | 25.2 ± 7 | | 21 | | | |
| Small body size/ruffled fur/hypoactive | 3.3[f] | 0/23 | 7/7 | 0/52 | 13/13 | 0/32 | 2/2 | 0/20 | 25/25 | 0/127 |

TABLE 1-continued

Incidence of disease in CD4C/HIV Tg mice

| | Mice Studied[b] | | | | | | | | | |
|---|---|---|---|---|---|---|---|---|---|---|
| | 15564 | | 17001 | | 17018 | | 17086 | | Total[e] | |
| Pathology observed[a] | + | −[d] | + | −[d] | + | −[d] | + | −[d] | + | −[d] |
| Diarrhea | 0/1 | 0/23 | 3/7 | 0/52 | 2/4 | 0/32 | 1/2 | 0/20 | 6/14 | 0/127 |
| Edema | 0/1 | — | 2/7 | 0/7 | 2/4 | 0/4 | 1/2 | 0/2 | 5/14 | 0/13 |
| Low body weight | 1/1 | — | 7/7 | 0/7 | 4/4 | 0/4 | 2/2 | 0/2 | 14/14 | 0/13 |
| Small/Absent Thymus | 1/1 | — | 7/7 | 0/7 | 4/4 | 0/4 | 2/2 | 0/2 | 14/14 | 0/13 |
| Small/Absent Lymph Nodes | 1/1 | — | 7/7 | 0/7 | 3/4 | 0/4 | 1/2 | 0/2 | 12/14 | 0/13 |
| Small "Pale" Spleen | 1/1 | — | 7/7 | 0/7 | 3/4 | 0/4 | 1/2 | 0/2 | 12/14 | 0/13 |
| Small &/or "Mottled" Kidney | 1/1 | — | 6/7 | 0/7 | 2/4 | 0/4 | 2/2 | 0/2 | 11/14 | 0/13 |
| Microscopic | | | | | | | | | | |
| Thymus: Hypoplasia[g] | | | 1/2 | 0/6 | 4/4 | 0/4 | 1/2 | 0/2 | 6/8 | 0/12 |
| Spleen: Hypocellularity[g] | | | 4/5 | 1/6 | 2–3/3 | 0/4 | 1/2 | 0/2 | 7/10 | 1/12 |
| Lymph Nodes: Hypocellularity[g] | | | 1/1 | 0/2 | 4/4 | N.A. | 0/1 | 0/1 | 5/6 | 0/3 |
| Kidney: Tubular interstitial nephritis | | | 6/7 | 0/7 | 2–3/3 | 0/3 | 1–2/2 | 0/1 | 9/12 | 0/11 |
| Lung: Interstitial pneumonitis | | | 1/6 | 0/5 | 3/4 | 0/4 | 2/2 | 0/1 | 6/12 | 0/10 |

[a]See the text for a detailed description of the disease.
[b]No. of mice with trait/total no. of mice assessed. The mice studied include the Tg founder itself as well as Tg (+) and non-Tg (−) offspring derived from each founder (F15564, F17001, F17018, F17086).
[c]Mean of age in days ± SD at which N1 animals died of disease or were sacrificed due to severe illness. A total of 3, 7, 13 and 2 mice from founder F15564, F17001, F17018 and F17086, respectively were assessed.
[d]For all Tg lines studied, non-Tg mice (−) were littermates of Tg mice kept in the same cages and sacrificed the same day as the Tg mice. Equal number of Tg and non-Tg mice were autopsied.
[e]Total animals assessed in all lines.
[f]Hypoactivity was not assessed in these 3 mice.
[g]Disorganized architecture accompanied hypocellularity in most organs assessed.

Pathological Assessment of CD4C/HIV Tg Mice

At autopsy, macroscopic observation revealed severe wasting, edema and abnormalities of several organs (lymphoid organs, kidney and lungs) in most Tg mice, as compared to control non-Tg littermates sacrificed at the same time (Table 1). Generally, when pathological changes were severe in one organ, other organs of the same mouse were also affected.

a) Wasting: Severe wasting (loss of both fat and lean body mass) was observed in all the Tg mice. The muscle mass was atrophic, no fat was visible and the bones (ribs) were thin and friable compared to normal animals of the same size.

b) Lymphoid organs: (Thymus, spleen, lymph nodes)

All lymphoid organs were atrophic. The thymus was either barely detectable or very small, containing 0.5 to 2.4×10⁶ cells (n=5) as compared to 25×10⁶ cells in control non-Tg littermates. The spleen was also very small [1.5 to 10×10⁶ cells (n=7) as compared to 30×10⁶ cells in control littermates] and pale (FIG. 2A). Panel A of FIG. 2 is a macroscopic view of spleens from non-Tg (bottom) and Tg (F17001, top) animals. Note the markedly smaller size, and paler color of the Tg mouse spleen. Panels B–G of FIG. 2 are light microscopic images of various lymphoid tissues. Panels B, C of FIG. 2: Non-Tg and Tg (F17001) spleens respectively, note the generalized loss of splenic architecture and hypocellularity in the Tg spleen. Panels D, E of FIG. 2: Non-Tg and Tg thymus (F 17018) respectively, note the tissue disorganization, small size and hypocellularity of the Tg thymus. Panels F, G of FIG. 2: Non-Tg and Tg lymph nodes (F17001) respectively, again there is a generalized loss of architecture and hypocellularity of the organ. Magnification: Panel A: , Panels B–E:90×, Panels F, G: 440×. Counter stain, Panels B–G, hematoxylin and eosin (FIG. 2).

Mesenteric lymph nodes were also smaller than in control non-Tg mice and contained fewer cells (0.1–0.4×10⁶ cells as compared to 9.4×10⁶ cells in control littermates). This atrophy of lymphoid organs was also observed in two animals kept in a specific pathogen-free (SPF) facility.

Figure 2C:
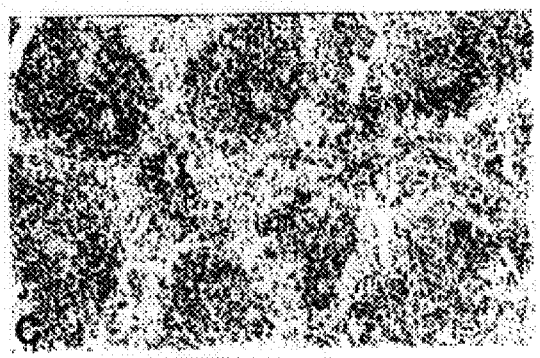
Figure 2D:
Figure 2E:
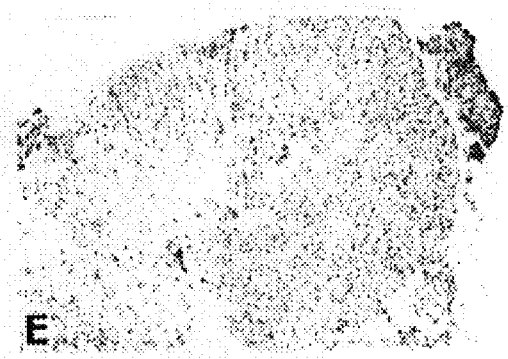
Figure 2F:
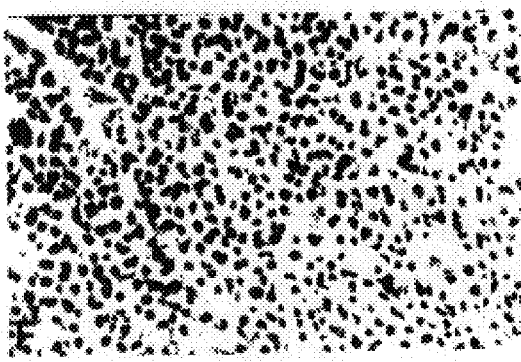
Figure 2G:
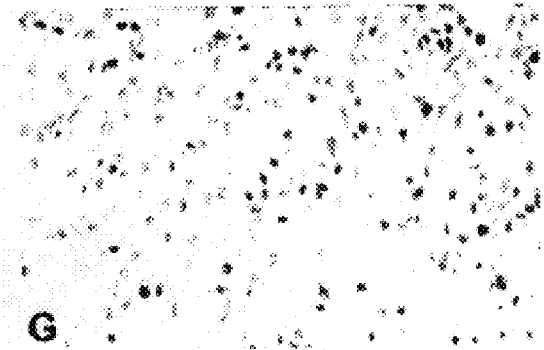

Histological examination revealed abnormalities in the spleen of a majority (7 out of 10) of Tg mice assessed from three lines (Table 1). This pathology consisted of partial to extensive loss of splenic architecture, frequent hypocellularity and occasionally fibrosis (FIG. 2C). When sufficient thymic mass was present for histological assessment, changes consisting of loss of architecture and hypocellularity were noted in a majority (6 out of 8) of mice assessed (Table 1, FIG. 2E). Finally, in a majority of Tg mice examined (5 out of 6) (Table 1), the mesenteric lymph node was hypocellular and its architecture disorganized (FIG. 2G). Lymphoid organs taken from non-Tg littermates exhibited normal histology (Table 1) with the exception of ¹⁄₁₂ spleens assessed which showed follicular regression. Thus similar if not identical histopathology was observed in the majority of lymphoid organs examined (18 out of 24 combined organs) of Tg mice from three independent CD4C/HIV founder lines, suggesting that this phenotype was transgene-specific.

c) Kidneys

In most Tg mice, kidneys were markedly atrophic and paler than in the control mice. In more severely affected mice, kidneys had an irregular surface which was less shiny (Table 1, FIG. 3A). Panel A of FIG. 3 is a macroscopic view of kidneys from non-Tg (left) and Tg (F17001, right) animals. Note the smaller size, and paler color of the tg mouse kidney. Panels B–C of FIG. 3 are light microscopic images, of kidney in longitudinal section, from normal (Panel B) and Tg (Panel C, F17018) . Note, the significant numbers of fluid filled dilated tubules and cystic areas. Panels D, E: Non-Tg and Tg (F17018) lungs respectively. Note the extensive interstitial pneumonitis in the Tg lung, and the lack of airway disease. Magnification:Panels B, C: 90×, Panels D, E: 220×. Counter stain, Panels B–E, hematoxylin and eosin (FIG. 3).

Figure 3A:
FIG. 3 illustrates the pathology observed in kidney and lung of CD4c/HIV tg mice; comparison to age matched non-tg control animals. Panel A is a macroscopic view of the kidneys from the non-Tg (left) and Tg (right) animals. Panel B is the non-Tg and panel C is the Tg longitudinal section of the kidney, illustrating dilated tubules and cystic areas in the Tg animal. Panel D is the non-Tg and panel E is the Tg lung, illustrating the extensive interstitial pneumonitis in the Tg lung.
Figure 3B:
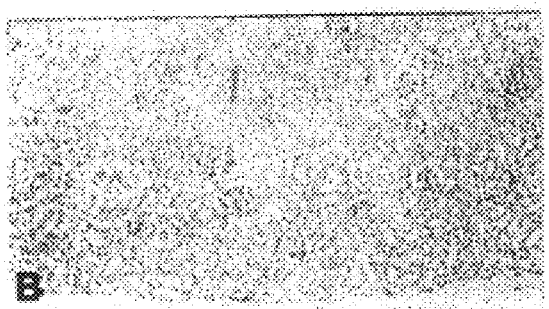
Figure 3C:
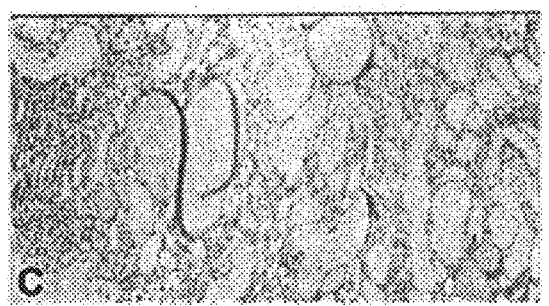
Figure 3D:
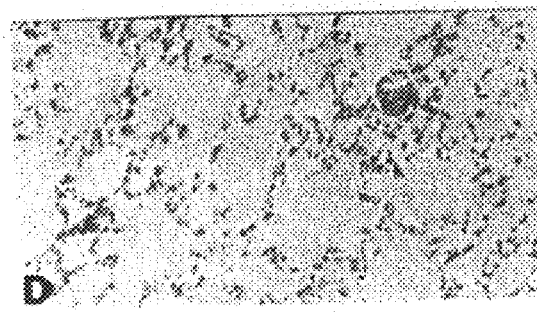
Figure 3E:
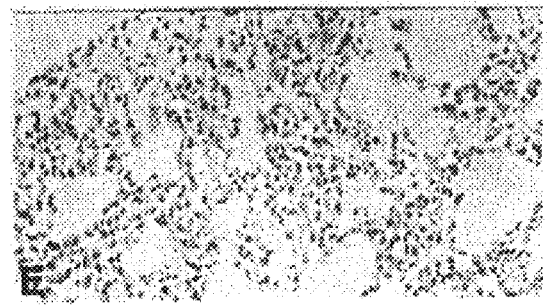

Five of these mice also exhibited edema, suggesting the presence of a nephrotic syndrome. Histologic examination showed the presence of an interstitial nephritis accompanied by tubular atrophy and dilatation (FIG. 3C) in a majority of mice examined (10 out of 14).

d) Lungs:

The lungs of Tg mice were firm as compared to those of non-Tg mice. Histological examination showed changes were due to a marked thickening of alveolar walls by infiltrating cells of lymphoid morphology in some Tg animals (FIG. 3E). Such severe interstitial infiltration was not observed in non-Tg littermates. No evidence of air-space disease was noticed in Tg mice. Two Tg mice with extensive lung disease were assessed for pneumocystis carinii infection by Grocott's stain of lung sections and were found negative.

FACS Analysis of Lymphoid Cells From CD4C/HIV Tg Mice

FACS analysis performed on thymocytes of 5 Tg mice from founder F17001 with antibodies against CD4, CD8 and TcR showed dramatic changes: the $CD4^+CD8^+$ and $CD4^+CD8^-$ cells were almost absent in all Tg mice, while $CD4^-CD8^+$ and $CD4^-CD8^-$ T-cells constituted the largest populations.

These two subpopulations usually represent a small fraction (5–6%) of thymocytes in normal mice. Interestingly, only a minority of thymocytes (<1%) were found to express TcR, an indication that the large population of remaining $CD4^-CD8^+$ thymocytes did not have the phenotype of mature T cells. A similar analysis carried out on spleen and lymph node cells of Tg mice showed very low percentage of mature $CD4^+$ (0 to 6%), $CD8^+$ T cells (1 to 3.8%) and a reduction in the number of TcR expressing cells (<3% vs control ~18%). Other N1 offspring (n=2) from other lines (F17018, F17086) showed a similar but variable depletion of $CD4^+$ T cells in peripheral lymphoid organs. Because of the low number of Tg mice which could be produced due to the high mortality rate, the study of the effect of HIV-1 expression on thymocyte populations during earlier stages of the disease could not be done.

A similar analysis was carried out on CD4A/HIV$^{wt}$ Tg mice which displayed considerably lower levels of transgene expression. No alteration of the T cell population (in terms of percentage or CD4/CD8 ratio) was detected in several animals (n=20) from three distinct lines. This suggests that a certain threshold of HIV-1 expression is required to elicit the perturbation of T cells observed in CD4C/HIV Tg mice. Together these results indicate that expression of HIV-1 in these mice profoundly affects the production and/or survival of T cells.

Expression of the Transgene in CD4C/HIV Tg Mice

Transgene expression was first assessed by Northern blot analysis of various organs of 20 day-old mice derived from three CD4C/HIV Tg founders. The three main transcripts of HIV-1 (8.8 kb full-length, 4.3 kb env-specific and the 2.0 kb multiply-spliced) were detected at high levels in thymus, and moderate levels in spleen and lymph nodes (FIG. 4). Northern blot analysis was carried out on total RNA (10 μg) extracted from different organs of mice from line F17018 (Lanes 1–12), F17001 (Lanes 13–18) and F17086 (19–32). Lanes 1, 16, 19: Kidneys; 2, 17, 20: Lymph nodes; 3, 13, 21: Thymuses; 4, 4, 22: Lungs; 5, 15, 23: Spleens; 6, 18: Livers; 7: Testis; 8: skin; 9: Intestines 10: Muscle; 11: Heart; 12: Brain; 24: RNA from mammary glands of a MMTV/HIV Tg mouse used as positive control. Length (kilobases) of the different spliced forms of HIV-1 is shown at the left. Hybridization was performed with $^{32}$P-labeled 8.9 kbp SacI fragment from the HIV-1 genomic sequences. (b) The filters were then washed and rehybridized with an actin probe.

These organs are known to support transcription of surrogate genes from this CD4C promoter. A weak but detectable signal was also observed in other organs such as kidneys, lungs, intestines and liver (FIG. 4). This hybridization signal could originate from circulating T lymphoid cells and/or resident macrophages, known to support the expression from this CD4C promoter (Hanna Z et al., Mol. Cell. Biol., 1994, 14:1084–1094). No expression was detected in testis, skin, muscle, heart and brain (FIG. 4).

Figures 5A, 5B, 5C:
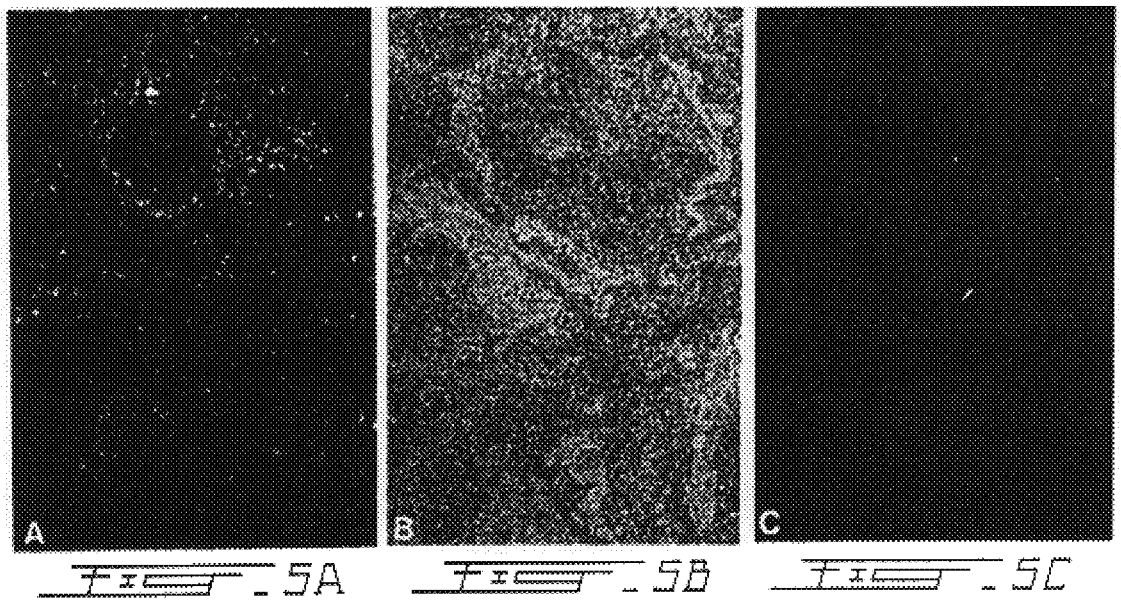
FIG. 5 illustrates the transgene expression assessed by in situ hybridization in lymphoid tissues of CD4C/HIV Tg mice. Panel A is a dark field image of Tg spleen illustrating T-cell expression of the transgene. Panel B is a bright field image of the filed shown in panel A. Panel C is a dark field image using the transgene sense probe as a control. Panel D and E are thymus sections from the Tg animal hybridized with an anti-sense transgene probe (panel D) and sense transgene probe as a control (panel E) illustrating the T-cell and macrophage specific expression of the transgene.

The distribution of transgene expression in different tissues from diseased mice sacrificed late in the disease was further evaluated by in situ hybridization (ISH) with $^{35}$S-labeled HIV-1-specific antisense and control sense riboprobes. On a per cell basis, moderate to strong expression of the transgene was observed in each of the four Tg lines in various organs assessed. In lymphoid tissues, expression was seen in diseased organs, but was rarely observed in normal appearing tissues, indicating that expression of HIV-1 gene products was correlated with development of pathological lesions. In the spleen, the numbers of Tg-expressing cells varied from several tens to hundreds per section. Because of the loss of tissue architecture, it was difficult to assign expression to white or red pulp areas. However, where present the Tg expression was concentrated in the red pulp areas (FIGS. 5A and 5B).

Figures 5D, 5E:
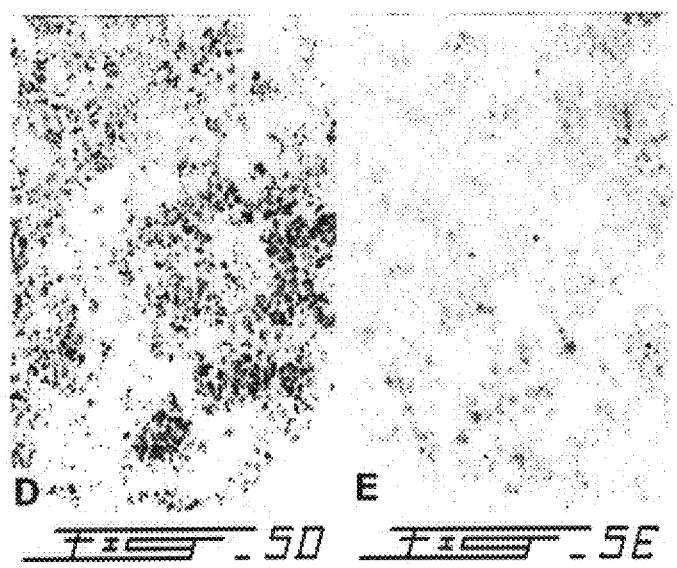

Panels A, and C of FIG. 5 are darkfield images of spleen (F17001). Panel B is the bright field image of field shown in panel A. Note the majority of transgene expressing cells are not in germinal centers where the highest concentrations of B cells are found, but are restricted to the marginal zone and red pulp of is the spleen, where the highest concentrations of T cells and macrophages are found. Panels D, E are thymus from a Tg animal (F17001). Tissue was hybridized with antisense probes, panels A, D or sense probe panels C, E. Note the absence of a cell specific hybridization signal in the sections exposed to the sense probe. Magnification Panels A–C: 90×; D, E: 360×. Counter stain, all panels, hematoxylin and eosin.

In the lymph nodes, again the disorganization of tissue architecture made it impossible to determine the localization of the expressing cells. In the thymuses whose architecture was not too distorted, Tg expression was found to be concentrated in the cortical region (FIG. 5D), while fewer medullary cells expressed the transgene, consistent with an expression in $CD4^+CD8^+$ (cortical and $CD4^+CD8^-$ (medullary) T cells. Interestingly, in some diseased spleens, thymuses and lymph nodes, no Tg expression could be detected, suggesting that the lesions were either induced indirectly or more likely that Tg expressing cells were already depleted in these mice.

Tg expression was also observed in non-lymphoid tissues. In five diseased kidneys, interstitial, most likely infiltrating mononuclear leukocytes (FIGS. 6A and 6C), located between the tubules and cells within glomeruli were found to express the transgene (FIGS. 6A and 6D). It was not possible to determine whether the cells within the glomeruli were normal components of the glomerulus, or were infiltrating cells, although cells around the periphery of glomeruli, where mesangial cells are located, often had elevated levels of transgene expression (FIG. 6A).

Transgene expression was detected in kidney (FIG. 6, Panels A–D, F17001), intestine (Panels E, F17018), liver (Panel F, F17001), and lung (Panel G, F17001). Panel A, darkfield image of kidney form an animal with extensive pathology, note expression of the tg in areas corresponding to glomeruli (arrowheads) as well as ductal regions. Note the higher concentration of silver grains at the periphery of the glomeruli, the location of mesangial cells. Panel B, sense probe control of the same tissue. Panels C, D, bright field images of interstitial infiltrating cells (Panel C) and glomerular cells (Panel D). Panels E–G: Tg expression is seen in cells of lymphoid morphology in the lamina propria of the intestine (Panel E) in liver Kupffer cells (Panel F) and in interstitial infiltrating cells and alveolar macrophages (Panel G,) in the lung. Magnification Panels A, B, E–G: 220×; Panels C–D:360×. Counter stain, all panels, hematoxylin and eosin.

Tg expression was undetectable in two further kidneys with minimal pathological changes and in one exhibiting normal morphology. These results strongly suggested that the kidney lesions in these mice were related to the number of cells expressing the transgene.

Tg expression was also observed in cells with a lymphoid morphology in several other organs, such as the lamina propria of the intestine (FIG. 6E), the livers and lungs. Liver Kupffer cells (FIG. 6F) and lung interstitial infiltrating cells and alveolar macrophages (FIG. 6G) were also found to express the transgene. In addition, peritoneal macrophages from a mouse of line F17001 were found to express the transgene, as expected. Other cell types not expected to express the Tg were negative by ISH. Thus, the epithelial cells, smooth muscle and connective tissue cells of the GI tract, epithelial cells of kidney, lung and liver, the myocytes of the heart and skeletal muscle, seminiferous tubules, spermatocytes as well as vasculature in these organs were all negative for Tg expression. Together, these results are consistent with the specificity of the CD4C promoter for $CD4^+$ T lymphocytes and for cells of the macrophage lineage.

Expression of the Transgene in CD4A/HIV Tg Mice

Transgene expression in thymuses and spleens of mice from different CD4A/HIV founders was barely detectable by Northern blot analysis.

However, it was demonstrated by RT-PCR analysis on total RNA extracted from the same lymphoid organs. The level of expression in CD4A/HIV Tg mice varied from line to line and was estimated to be ~20–60 fold lower than in CD4C/HIV Tg mice.

Studies of CD4C/HIV Chimeric Mice

The lethal diseases induced in young mice by the expression of the CD4C/HIV transgene prevented the establishment of Tg lines. Because the Tg founders which were mosaic survived longer than their non-mosaic Tg offspring, we decided to generate chimeric CD4C/HIV Tg mice. Possibly, these animals would remain viable for a longer period of time and may develop pathologies resulting from a more chronic exposure to HIV-1 gene products. Cells from ES cell clones harboring the transfected CD4C/HIV transgene (J1-1838-2 and J1-1838-5) were used to generate chimeric mice by inoculation into C57BL/6 blastocysts. Twelve and fifteen out of 35 and 21 born mice respectively showed coat color chimerism.

Southern blot analysis with an HIV-1 probe also demonstrated variable contributions of ES cells to multiple tissues. Five out of 15 chimeric mice derived from clone J1-1838-5 exhibited disease early in life and were sacrificed at 18–32 days after birth. This disease was similar to that described above for CD4C/HIV Tg mice. The phenotype included low body weight [6 to 8 g (n=4) as compared to 13 g for aged-matched non-chimeric controls], wasting, slow movement, hypoactivity and early death. This phenotype was not observed in non-chimeric mice, suggesting that it was transgene-specific.

Transgene expression was assessed by in situ hybridization on several tissues (lung, kidney, spleen, lymph node, thymus) of chimeric mice. Among the eight chimeric mice derived from clone J1-1838-2, which were studied, only one animal (#22397) showed any evidence of transgene expression: a few cells per section were positive for transgene RNA in spleen, thymus and lymph node. None of these animals showed any evidence of pathology in their tissues. These results suggest that the absence of a phenotype in these chimeric mice may be related to the low levels of transgene expression. However, RT-PCR performed on peritoneal macrophages isolated from 3 chimeric animals indicated that there was expression in these cells, and this was confirmed by in situ hybridization in one animal.

In contrast, five chimeric mice derived from clone J1-1838-5 harbored HIV-1 expressing cells in several organs and the expression per cell was relatively high: the intensity of the in situ signal was comparable to that observed for Tg animals. The number of in situ positive cells per tissue section varied from less than 100 to more than 1000. Generally, higher number of positive cells were correlated with histopathology. In three animals (#20882, 20886, 20887), transgene expression was observed in the kidneys, in cells of several glomeruli as well as in interstitial mononuclear leukocytes.

The tissue distribution and histological location, of Tg expression in chimeric mice, was indistinguishable from that observed in the normal Tg animals. Expression was detected in thymus, spleen Intestine, and Kidney.

Two of these mice (#20886, 20887) showed clear evidence of kidney disease. The pathology observed was indistinguishable from that observed in the CD4C/HIV Tg animals. Here, greater pathology was observed in the animal (#20887) exhibiting the highest number of in situ positive cells. Three chimeric mice (#20883, 20886, 21075) had detectable transgene expression in the thymus and one of these (#20883) exhibited histopathology consisting of a loss of a clear cortico/medullary junction. A further two of these animals (#20883, 20886) had splenic expression of the transgene, and one of the three animals (#20886) exhibited lymph node expression. No detectable pathological lesion was observed in any of these lymphoid tissues. Large bowel pathology was observed in 1 of 7 chimeric animals (#20887) assessed. This consisted in lymphoid hyperplasia of the mucosa and transgene expression in the mucosa. Two out of eight chimeric mice (#20886, 20887) also had severe pneumonia and infiltrating cells in one animal (#20886) expressed the transgene.

Together, these results extend and confirm our data on the mosaic founder mice. They show that high numbers of cells expressing moderate to high levels of this transgene are correlated with pathology.

Overexpression of RANTES in CD4C/HIV Tg Mice

HIV-1 infection has been found to upregulate β-chemokine expression in monocytes in vitro and in vivo. To determine whether the expression of β-chemokines was affected in CD4C/HIV Tg mice, we measured PANTES expression in several lymphoid and non-lymphoid tissues of Tg mice using in situ hybridization. In 4 of 7 Tg animals examined, moderate to high numbers of RANTES-expressing cells were detected in lymphoid (thymus, spleen and lymph nodes) as well as in some non-lymphoid (in cells of the lamina propria of the GI tract and interstitial cells infiltrating the kidney) tissues. Higher numbers of RANTES-expressing cells were observed in the lymph nodes (FIGS. 7A to 7C), and in non-lymphoid tissues (FIGS. 7D and 7E).

Elevated levels of expression of the chemokine RANTES were detected in tg animals with the same general tissue distribution and histological location as observed for the tg expression. Panels A–C of FIG. 7: Lymph node, the same field in darkfield (Panel A) and bright field (Panel B), showing tissue hybridized with antisense probe, panel C is the same region of the node exposed to the control sense probe (F17018). Note the hypocellularity of the node in Panel B. Panel D: cells of the lamina propria of the intestine (F17001). Panel E: Interstitial cells in the kidney (F17001). Magnification Panels A–C: 220×; D:720×. Counter stain, all panels, hematoxylin and eosin (FIG. 7).

The increased expression of RANTES was not observed in control non-Tg littermates in which only very low levels (occasional expressing cells) of RANTES expression were detected in lymphoid tissues. These results suggest that RANTES may play some role in the HIV-1 induced changes seen in these mice.

Expression of the Transgene in Target Cells for HIV-1 Infection

Our results show that Tg mice expressing the complete HIV-1 coding sequences under the regulation of the CD4C promoter develop a severe AIDS-like disease followed by early death. It was previously reported that this promoter, derived from the human and mouse CD4 genes, allows expression of surrogate genes in $CD4^+CD8^+$ and $CD4^+$ thymocytes, in peripheral $CD4^+$ T cells and macrophages (Hanna Z et al., Mol. Cell. Biol., 1994, 14:1084–1094). Expression of the transgene in CD4C/HIV mice was found to be in the same cells, namely T-cells and macrophages. In addition, we have also recently documented in further examination of CD4C/CD4 Tg mice that this promoter is active in spleen dendritic cells. These represent the specific subsets of cells which are normally targeted for infection by HIV-1 in humans (Schnittman S M et al., Science, 1989, 245:305–308). Expression of HIV-1 in these specific cell populations of Tg mice appears important to elicit this AIDS-like disease since other mice similarly expressing the whole HIV-1 genome at high levels in different cell populations through different promoters did not develop any apparent phenotype of the immune system. Although both the T cells and the dendritic/macrophage cell lineages are expressing the HIV-1 genome in the CD4C/HIV Tg mice, it is not clear whether expression in each of these lineages is required for induction of each of the phenotypes observed. In fact, expression of HIV-1 in dendritic/macrophage cells may be sufficient to elicit several of the phenotypes seen in these mice. On the other hand, expression of specific factor by HIV-1 expressing $CD4^+$ T-cells may be an absolute requirement for development of some or all phenotypes. Additional work is needed to approach this question.

The identity of the HIV-1 gene(s) responsible for inducing disease is not known since the CD4C/HIV transgene used in the present study has the capacity to code for all the HIV-1 proteins. A single gene product or a combination of some HIV-1 gene products may be responsible for the several pathological lesions observed in different organs. Construction of additional Tg mice with several HIV-1 mutants will be required to identify the HIV-1 gene(s) responsible for each pathological change (see below).

To date, only mice from another Tg line expressing the whole HIV-1 genome under the regulation of the HIV-1 LTR have been reported to develop an AIDS-like disease characterized by early death and pathological changes in several organs (Leonard J M et al., Science, 1988, 242:1665–1670). Some of these changes were similar (early death, lymphadenopathy, thymus hypoplasia, lung lesions) to those seen in CD4C/HIV Tg mice, while others were different (epidermal hyperplasia, absence of detectable HIV-1 RNA in spleen by ISH) or absent (kidney disease). However, only one line (No. 13) of Tg mice developed this disease, and an insertion mutation by the transgene may have contributed to the phenotype.

Viral Load and Development of Diseases

Beside the specific cell populations in which the transgene is expressed in CD4C/HIV Tg mice, the level of HIV-1 expression is another parameter which may have influenced the development of disease in these mice. In these Tg mice, the levels of gene expression are determined by the levels of transcription achieved in each line and by the number of cells expressing the transgene in mosaic Tg mice. It appears that a relatively high viral RNA load was required for the development of the disease. Four out of five Tg founder mice which were mosaic for the transgene, and presumably had lower number of HIV-1 expressing cells, failed to develop disease or developed the disease much later than their non-mosaic N1 offspring. Similarly, only chimeric mice expressing the highest number of HIV-1 expressing cells developed disease. In addition, the CD4A/HIV Tg mice, which expressed HIV-1 at much lower levels did not develop disease even after a long period of observation. Therefore, as in human AIDS, the viral RNA load appears to be a primary determinant of disease in CD4C/HIV Tg mice. Since no reinfection cycle occurs in these mice, this viral RNA load is likely to mimic a steady-state load of virus expression in humans.

AIDS-like Pathologies in Tg Mice

The choice of the CD4C promoter to express HIV-1 gene products at relatively high levels in our study has allowed the development of several pathological changes which are similar to those found in individuals with AIDS, and especially in pediatric AIDS, consistent with the fact that the transgene is expressed early in life. The most dramatic outcome of the expression of the transgene in these mice is early death, also seen in a high percentage of infants (Scott G B et al., New England J. of Medicine, 1989, 321:1791–1796) and in some adults with AIDS. We have been unable to identify the exact cause of death except in some mice with a severe lung disease or kidney disease associated with a nephrotic syndrome. For most animals, a few obvious causes of death appear to be less probable. Death is unlikely to result only from bacterial or viral infections occurring in these immunodeficient mice which have lost most of their lymphocytes, since early death was also observed in two animals kept in an SPF facility. Death is also unlikely to be exclusively the result of the loss of T cells, since nude mice kept in the same rooms survived much longer than these CD4C/HIV Tg mice. The kidney or lung diseases cannot account either for all of these early deaths since severe and life-threatening kidney or lung lesions were not present in all mice which died early. This early death may have several causes, and in particular may be related to the severe wasting observed in the majority of these mice. In HIV-1 infected humans, wasting has been found to be a strong predictor of survival.

Wasting indeed represents the second most striking phenotype in these mice. It has been described in a relatively high percentage of AIDS patients in Western countries (Coodley G O et al., J. of Acquired Immune Deficiency Syndromes, 1994, 7:681–694). In some parts of the world, and especially in Africa, it represents one of the most apparent signs of AIDS, which is designated "slim disease". The pathogenesis of this AIDS-associated wasting is not well understood, but it is thought to be multifactorial. It resembles the cachexia seen in cancer and it has been postulated to be related to an immune activation state and to the production of cytokines. A similar cachexia syndrome has been described in one line of Tg mice expressing the 3' half of the HIV-1 genome (Santoro T J et al., Virology, 1994, 201:147–151). However, it was observed only in mice homozygote for the transgene and may have resulted from an insertional mutation by the transgene. Therefore, the wasting seen in the heterozygote CD4C/HIV Tg mice represents the best model yet available of HIV-1-associated wasting in humans.

The third striking phenotype observed in these Tg mice is the small size of the lymphoid organs, the loss of their normal architecture accompanied by a severe depletion of thymocytes and peripheral T cells. Interestingly, the loss of the thymus mass appears progressive and is detectable later in the disease when the animals died or when they were sacrificed due to severe illness. Severe premature involution of the thymus with depletion of both lymphoid and epithelial thymic cell populations, and specifically of Hassall's corpuscules, is a feature of pediatric and adult AIDS in humans (Joshi V, Pediatric Hematology & Oncology, 1994, 11:351–355). In the thymus of the Tg mice, $CD4^+CD8^+$ immature and $CD4^+CD8^-$ mature T cells appear to be initially preferentially lost. Human $CD4^+CD8^+$ thymic T cells have been reported to be infectable with HIV-1 in vitro. The loss of T cells in peripheral organs of these mice is likely to reflect the virtual absence of precursor T cells in the thymus. Recent evidence indicates that a reduction in early life of both $CD4^+$ and $CD8^+$ T-cells in HIV-1 infected children (a DiGeorge-like immunophenotype) is associated with a rapid progression of AIDS. The loss of the architecture of the spleen and lymph nodes associated with fibrosis and hypocellularity also mimics the lymphoid organs of adults and especially children with advanced AIDS (Joshi V, Pediatric Hematology & Oncology, 1994, 11:351–355). The enlargement of lymph nodes was not observed in these Tg mice, a frequent pathological manifestation of early HIV-1 infection in human adults. However, in human pediatric AIDS, enlarged lymph nodes are not always observed and atrophy of the lymph nodes with severe lymphocytic depletion of the entire lymph node is not infrequent, especially at the late stage of the disease (Joshi V, Pediatric Hematology & Oncology, 1994, 11:351–355). In addition, the course of the disease in these young mice may be too rapid to observe enlargement of the lymphoid organs. Thymic atrophy and loss of T cells in peripheral lymphoid organs have previously been reported in Tg mice expressing only the HIV-1 nef gene under the regulation of T cell-specific promoters, suggesting that the thymic phenotype in the CD4C/HIV Tg mice may be primarily caused by the expression of the nef gene in T cells. The construction of additional Tg mice expressing mutant HIV-1 genomes is underway to test this hypothesis.

The fourth most important pathology seen in these Tg mice affects the kidneys. Kidney disease in AIDS patients is relatively frequent, particularly in children (Strauss J et al., New England J. of Medicine, 1989, 321: 625–630). A broad spectrum of renal lesions have been described including focal and segmental glomerulosclerosis, mesangial hyperplasia, tubulointerstitial nephritis (with tubulointerstitial cell infiltrates edema and fibrosis, accompanied by dilated tubules forming cysts), but the pathogenesis of these changes is not well understood. In the CD4C/HIV Tg mice, the predominant features of the kidney disease (tubulointerstitial nephritis) mimics what has been frequently observed in humans. Expression of the HIV-1 transgene in glomerular and tubular epithelial kidney cells was not expected to occur with the CD4C promoter used here. In fact, most of the cells expressing the transgene in the kidney appear to be infiltrating interstitial cells, some with a lymphocyte cell morphology. Cells of the macrophage lineage which express the transgene are also likely to be present in the kidneys. Surprisingly, glomerular cells were also found to express the transgene. This is consistent with the suggestion that glomerular cells may express CD4 in human and that HIV-1 nucleic acids and p24 protein have been detected in renal glomerular and tubular epithelium of patients with HIV-1 associated nephropathy. Therefore the pattern of transgene expression and the documented cell-specificity of the promoter itself suggest that the kidney disease may be caused by the expression of the transgene in renal epithelial and non-epithelial (most likely in T lymphoid cells and macrophages) cells, and that the pathogenesis of this kidney disease may be both indirect and/or direct. A role for macrophages in HIV-1 associated kidney diseases has previously been postulated. In addition, the expression of HIV-1 gene products may directly affect epithelial kidney cells. A severe kidney disease has previously been found to develop in Tg mice expressing the 3' half of the HIV-1 genome under the regulation of the HIV-1 LTR (Klotman P E et al., AIDS, 1995, 9:313–324). The kidneys were larger than non Tg-controls and most of their glomeruli were severely sclerotic. In contrast, in CD4C/HIV Tg mice, the kidneys were smaller than normal and glomerulosclerosis was rare and tubulointerstitial nephritis was the histological change most frequently observed. Since the identity of the cell population expressing the 3' half HIV-1 transgene in these mice was not reported, it is unclear whether the pathogenesis of the kidney disease in these Tg mice and in the CD4C/HIV Tg mice is the same.

The lung lesions constitute the fifth main phenotype detected in these Tg mice. It does not seem to be caused by pneumocystis carinii which was negative in these tissues. It resembles the pulmonary lymphoid hyperplasia/lymphoid interstitial pneumonitis described in children, and rarely in adults, with AIDS (Joshi V, Pediatric Hematology & Oncology, 1994, 11:351–355) and whose origin is unknown, but is thought to be immune-mediated.

Finally, the overexpression of RANTES in various tissues of these Tg mice represents a sixth phenotype which may be relevant to the human disease. Although MIP-1α and MIP-1β have been the main β-chemokines found to be elevated in HIV-1 infected monocytes, RANTES and other β-chemokines appear to represent the major soluble factors responsible for HIV-1 suppressive effects secreted by $CD4^+$ and $CD8^+$ T cells derived from HIV-1 infected individuals. Overexpression of RANTES may also have, by itself, detrimental effects in some tissues. In addition, high levels of RANTES would be expected to compete with the macrophage-tropic HIV-1 virions for the CCR-5 receptor and thus exert a strong selection pressure for the emergence of T-cell variants of HIV-1 utilizing another co-receptor, such as CXCR4/fusin. Our results suggest that this may be amenable to experimentation in vivo.

In summary, our results show that the expression HIV-1 gene products in specific subsets of cells which are normally targeted for HIV-1 infection in humans can be particularly pathogenic in mice, suggesting a specific response of these cells to the HIV-1 gene products. These mice developed a systemic disease characterized by several pathological changes strikingly similar to those observed in human AIDS. Such a constellation of pathologies has not been reported in other Tg mice expressing HIV-1 through different promoters, except in a single line (No 13) derived by Leonard et al. (Leonard J M et al., Science, 1988, 242:1665–1670). Therefore, the CD4/HIV Tg mice described here represent the best model of Tg mice yet available to date for human AIDS.

II) Mutant HIV-1 Genes

Generation of Tg Mice Harboring Mutant HIV-1 Genes

Figure 8A:
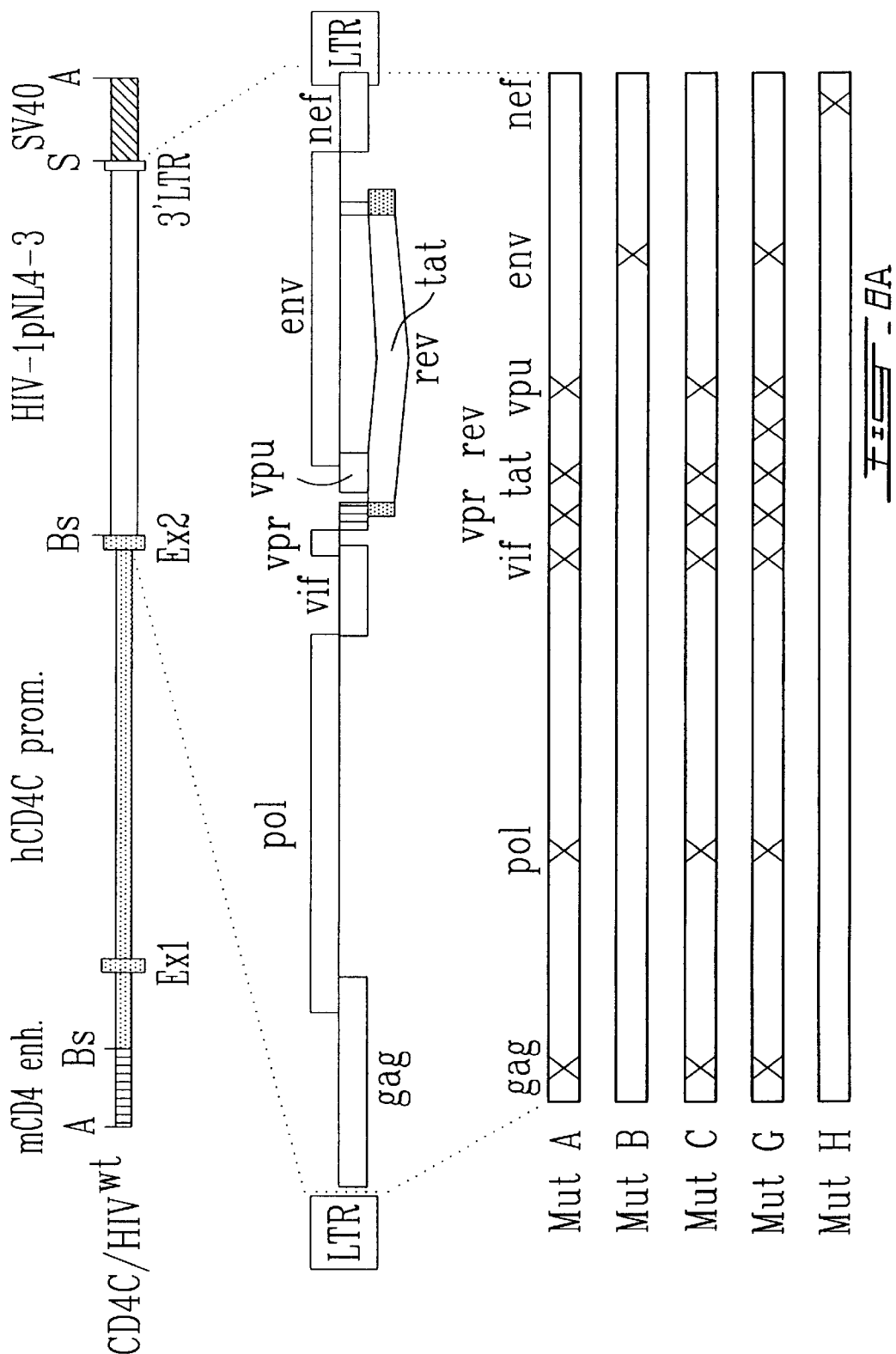
FIG. 8A illustrates the structure of the CD4C/HIV$^{Mut}$ transgenes.

Tg mice expressing HIV-1 different genes were produced (FIG. 8). The same regulatory elements of the human CD4 gene (CD4C) used above were used to drive the expression of this DNA. CD4C/HIV$^{MutG}$ has only the nef ORF left intact and all the other genes being mutated. In the construct CD4C/HIV$^{MutH}$, only the nef ORF was mutated and all other ORFs remained intact. Tg mice were produced with each of these DNA constructs. All founder (F) mice were bred on the C3H background and progeny mice were genotyped and routinely examined for signs of disease. At least 2 to 4 Tg mouse lines were established for each HIV-1 Tg mutant.

The CD4C/HIV$^{Mut}$ transgenes were constructed by mutating the NL4-3 HIV-1 genome of the CD4C/HIV$^{wt}$ transgene described earlier (Hanna, Z et al., J. Virol., 1998, 72:121–132).

The CD4C/HIV$^{MutG}$ transgene was constructed from mutant A by interrupting the rev and env genes by introducing the <<stop oligo>> at the SacI (nt 6003) and NdeI (nt 6400) site, respectively. The CD4C/HIV$^{MutA}$ transgene was generated by the addition of a 14-mer oligonucleotide containing three stop codons in each open reading frame (ORF) (5'-CTAGTCTAGACTAG-3', <<stop oligo>>), at the SphI (nucleotide (nt) 1447) and NdeI (nt 5123) sites of HIV-1$^{NL4-3}$ to produce gag and vif mutant genes, respectively. This oligo contains a XbaI site allowing the screening of mutated clones. The pol gene was mutated by deleting the 22 base pair (bp) HincII fragment (nt 2498 to 2521) followed by addition of the <<stop oligo>> at this site. The genome with vpr or vpu gene mutation (deletion of nt 5622–5737 and nt 6062–6180, respectively) were already available in plasmids p210–19 and p210–13 constructed previously and were obtained through the AIDS Research and Reference Reagent Program, National Institutes of Health. The tat mutation was produced by PCR site-directed mutagenesis with mutation primer 297 (5'-CCAGGGCTATAGTCTAG-3'), containing G to T mutation at nt 5854, creating a stop codon.

The CD4C/HIV$^{MutH}$ transgene was generated by ligating the 6.5 kbp BssHII-NheI HIV-1 fragment from the CD4C/HIV$^{wt}$ DNA with the 3'-end 3.2 kbp NheI-AatII fragment of the mutant C DNA containing the nef mutation.

All mutations were screened by XbaI digestion whenever possible and confirmed by sequencing. All transgene DNAs were isolated from the vector by AatII digestion and purified as described previously (Hanna, Z et al., J. Virol., 1998, 72:121–132). Tg mice were produced and bred as hetrozygotes with C3H mice as described before.

Clinical Phenotypes of CD4C/HIV$^{Mut}$ Mice

A clinical disease very similar to the one described in the CD4C/HIV$^{wt}$ Tg mice and leading to death (Hanna, Z et al., J. Virol., 1998, 72:121–132) developed in mice originating from 2 or more founders harboring the CD4C/HIV$^{MutA}$ or CD4C/HIV$^{MutG}$ DNA. The diseases induced by these three DNAs were indistinguishable and appeared similar, but exhibit a distinct latent period and penetrance according to the levels of Tg expression (see below). A high proportion (≈38%) of high-expressor mice had diarrhea and edema and most (>90%) developed weakness, hypoactivity and loss of body weight (wasting). Wasting was the most prevalent phenotype observed in these high-expressor mice. At 3 weeks of age, the body weight of non-Tg and Tg mice from different founders (MutA, F21407) was indistinguishable [non-Tg: 11.2±3 g (n=5); Tg=10.5±2.2 (n=11)]. However, by the end of the fourth week, in more severely affected mice, the body weight of Tg mice (8.7±1.7g) (n=11) was much lower than that of non-Tg littermates (17.9±3.3 g) (n=5). In mice expressing moderate levels of the Tg, these phenotypes appeared less frequently and later in life. None of the control non-Tg littermates (n=514) kept in the same cages as the Tg mice nor those mice harboring the CD4C/HIV$^{MutH}$ Tg (n=145) developed a similar disease.

CD4C/HIV$^{MutG}$ Tg Mice

To extend these data and confirm that indeed the nef gene was implicated in this disease, Tg mice harboring only the nef gene intact were constructed. Six founders were obtained and Tg line could be established with four founders (F26985, F27011, F27367 and F27372) but not from founders F26990 and F27357 whose offspring died at an early age. offspring from all founders, except from F26985, developed a disease similar to that observed in CD4C/HIV$^{MutA}$ mice. The latency of disease appearance varied among different lines (in the order F26990>>F27367>>F27011>F27372>F26985) according to the levels of HIV-1 expression (see below, FIG. 9). This latency was very short (30–50 days) in mice from founders F26990 (FIG. 8B) and F27357 expressing the Tg at highest levels (see below). The absence of an obvious phenotype in mice from founder F26985 is likely to reflect the low level of Tg expression in this line (see below) . The development of this severe disease in CD4C/HIV$^{MutG}$ mice, harboring a single HIV-1 gene intact, the nef gene, indicated that nef is necessary and sufficient to cause this phenotype.

CD4C/HIV$^{MutH}$ Tg Mice

To confirm that all the HIV-1 genes other than nef had a limited contribution in the development of these phenotypes, we produced the CD4C/HIV$^{MutH}$ Tg mice, with the complete HIV-1 coding sequences intact and only the nef gene mutated. Four founders were obtained (F37434, F37435, F37437 and F37441) and Tg lines were established. Although the levels of Tg expression in some of these lines were as high as those found in other lines developing disease (FIG. 9), no obvious phenotype could be detected in these Tg mice (n=70) during a 10-month latency period. This result confirmed our previous observations that nef harbored the primary determinant of pathogenicity in these Tg mice, and that the other HIV-1 genes were dispensable for the appearance of the phenotype.

Tg RNA Expression in CD4C/HIV$^{Mut}$ Mice

Northern blot analysis showed that the three main transcripts of HIV-1 (8.8 kb full-length, 4.3 kb env-specific and the 2.0 kb multiply-spliced) were detected at higher levels in the lymphoid than in non-lymphoid organs, in all Tg mutant mice. The Tg expression was correctly regulated in all founders, being consistent with the tissue specificity of this CD4C promoter (Hanna Z et al., Mol. Cell. Biol., 1994, 14:1084–1094). Weaker Tg expression was detected in kidney, lungs, intestine and liver and most likely reflected expression in T lymphocytes and/or resident macrophages, as previously documented (Hanna, Z et al., J. Virol., 1998, 72:121–132) and as reconfirmed in the present study (see below). Expression was not detected in testis, skin and muscle. This pattern of expression was indistinguishable from that observed previously in CD4C/HIV$^{wt}$ mice (Hanna, Z et al., J. Virol., 1998, 72:121–132). As expected, the levels of Tg RNA expression varied from founder line to another, most likely reflecting a positional effect at the site of Tg insertion.

Despite relatively high levels of Tg RNA expression, CD4C/HIV$^{MutH}$ mice remained healthy. However, an excellent correlation between the levels of Tg RNA expression and the time of death was observed in mice from the CD4C/HIV$^{MutA}$ and CD4C/HIV$^{MutG}$ lines.

Tg HIV-1 Protein Expression in CD4C/HIV$^{Mut}$ Mice

Figure 8B:
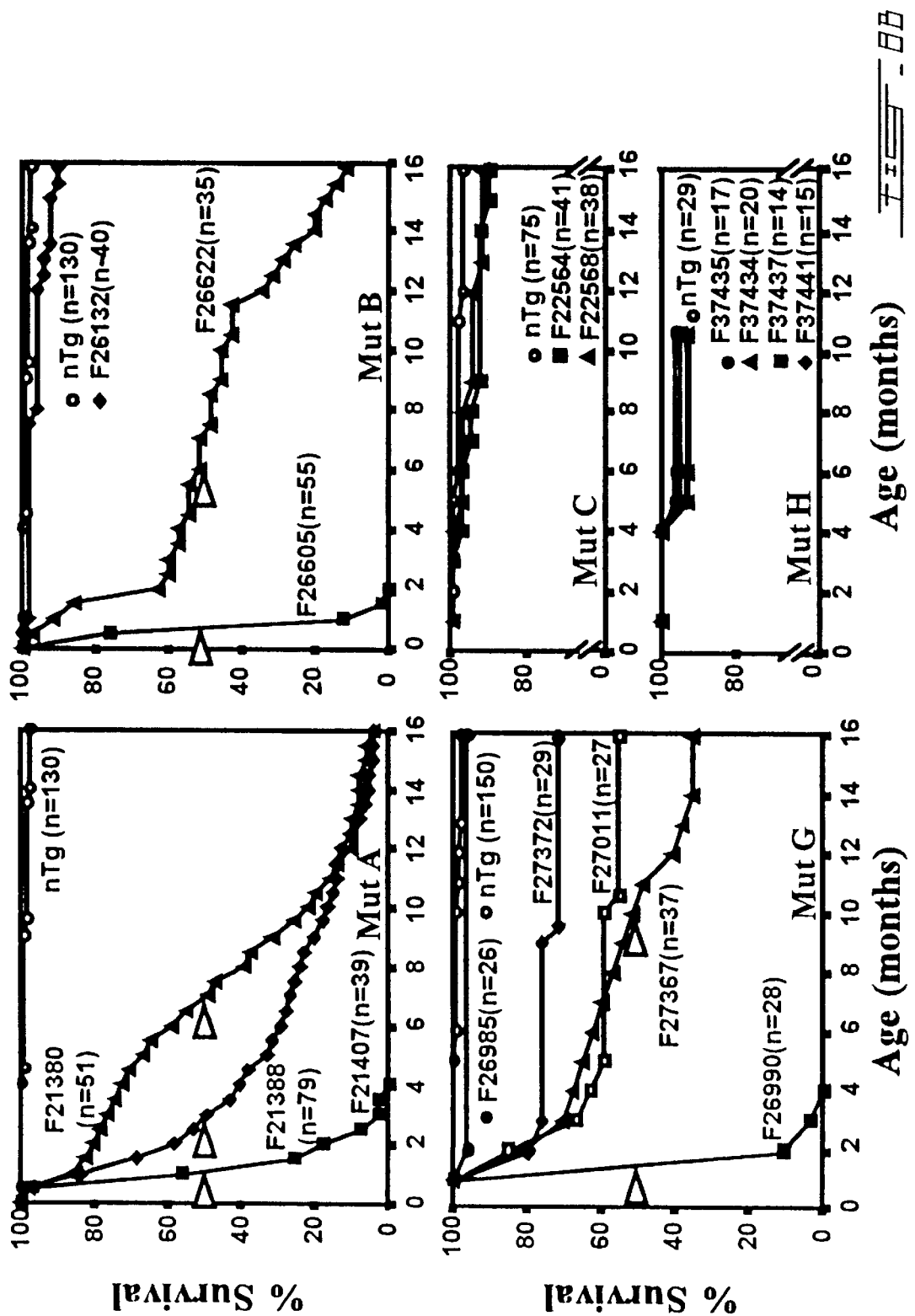
FIG. 8B illustrates the cumulative incidence of death in control non-Tg and CD4C/HIV$^{Mut}$ Tg mice.
Figure 9E:
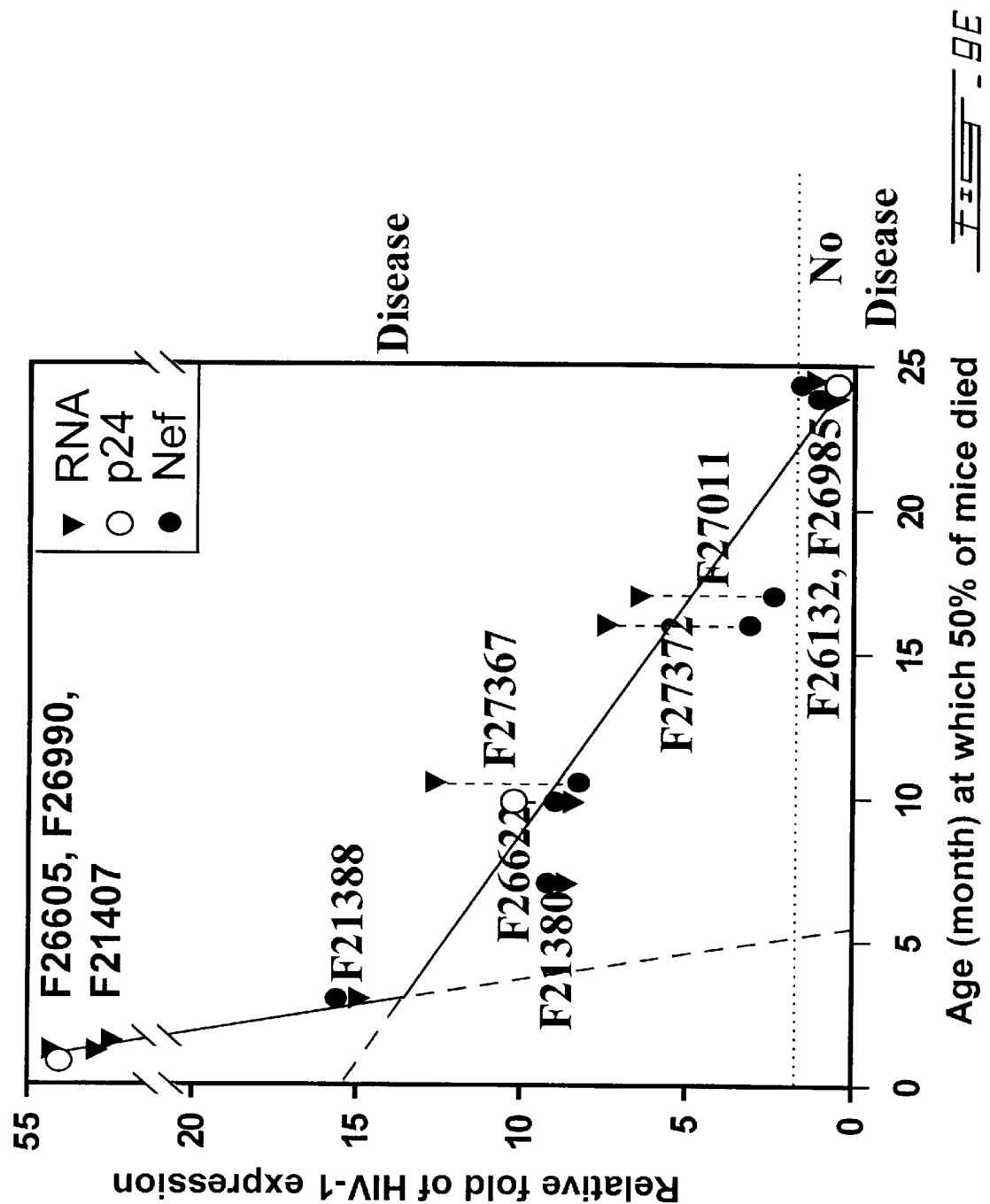
FIG. 9E illustrates the correlation between the time of death (TD$_{50}$) of CD4C/HIV$^{MutA}$, CD4C/HIV$^{MutB}$ and CD4C/HIV$^{MutG}$ Tg mice.
Figure 10A:
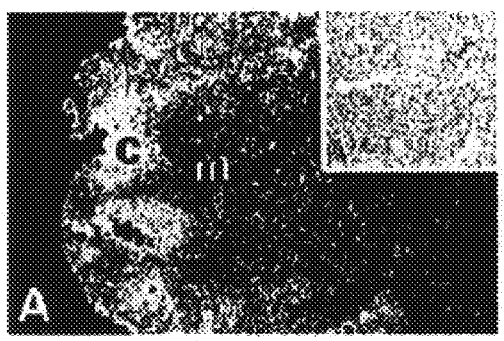
FIG. 10 illustrates the detection of Tg expression in CD4C/HIV$^{Mut}$ Tg mice by ISH. Panel A illustrates the thymic expression of the Tg was most concentrated in the cortical region. Panel B illustrates the spleen expression of the Tg was concentrated in the red pulp and marginal zone of the white pulp. Panels C–G and I illustrate Tg expression in other tissues; panel C illustrates expression in peritoneal macrophages, panel D illustrates expression in the lamina propria of the intestine, panel E illustrates expression in kidney infiltrating macrophages, panel F illustrates expression in cells found in the glomeruli, panel G illustrates expression in lung alveolar macrophages, and panel I illustrates expression in the liver. Panel H illustrates the lack of transgene expression in B-cells.
Figure 10B:
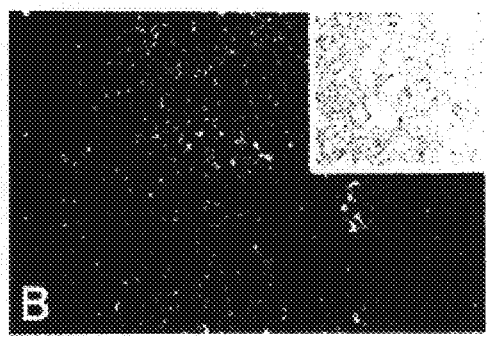
Figure 10C:
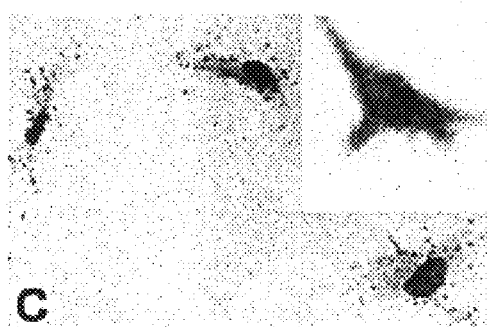
Figure 10D:
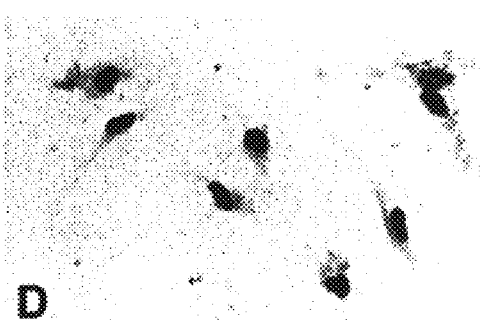
Figure 10E:
Figure 10F:
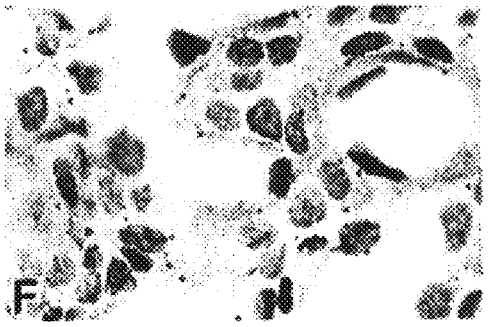
Figure 10G:
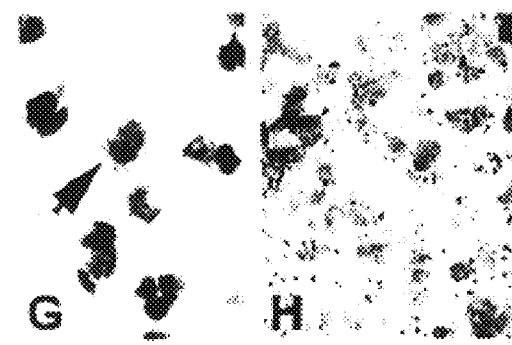
Figure 10H:
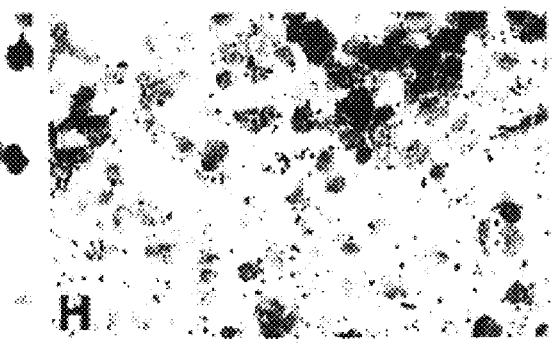
Figure 10I:

To examine Tg protein expression, Western blot analysis of lymphoid organs from different mutant mice was first performed with anti-nef and anti-env antibodies. This analysis revealed the presence of the expected gp160 and gp120 HIV-1 env proteins in lymphoid organs of CD4/HIV$^{MutA}$ and CD4C/HIV$^{MutH}$ Tg mice. Similarly, the Nef protein was detected in the same tissues of mice harboring an intact HIV-1 nef gene (CD4/HIV$^{MutA}$ and CD4C/HIV$^{MutG}$), as expected. These HIV-1 proteins could not be detected in target organs of mice harboring a mutated gene. In Tg mouse lines expressing lower levels of Tg RNA, HIV-1 env and Nef proteins could not be detected by this method. Detection of the HIV-1 gag CA(p24) protein was performed by ELISA on thymuses and spleens of mice from the CD4C/HIV$^{MutB}$ and CD4C/HIV$^{MutH}$ lines, the only lines harboring an intact gag gene. As expected, HIV-1 p24 was detected in mice from each CD4C/HIV$^{MutB}$ and CD4C/HIV$^{MutH}$ founder line and higher levels were observed in lines expressing higher levels of Tg RNA (FIG. 9D). These results indicated that the expected HIV-1 proteins were produced in these Tg mice. Tg expression correlates with the latency of disease The detection of higher levels of Tg RNA in lines exhibiting the most acute phenotype suggested that the levels of Tg expression was an important biological parameter. To further document this correlation, we quantitated the levels of HIV-1 RNA and Nef protein in the thymuses of mice from the CD4C/HIV$^{MutA}$ and CD4C/HIV$^{MutG}$ lines. The latency of the disease was evaluated by the time of death (TD50) of the Tg mice, as shown in FIG. 8B. A very strong correlation was observed between the levels of RNA, Nef (or p24) proteins and the TD50 values for the Tg mice (FIG. 9E). The data appear to fit a biphasic curve, indicating that below a certain protein level (arbitrarily defined here as 14-fold or ~135±50 pg p24/mg of total thymus protein), the rate at which disease developed was relatively slow. However, above this level, disease progression was much faster and followed a very steep curve, with a different kinetics. Furthermore, a second threshold of Tg expression seemed to be required for the development of an apparent disease within one year, as mice from CD4C/HIV$^{MutG}$ F26985 did not die in the first year of their life, despite having some Tg expression. Therefore, our mutational analysis coupled with these semi-quantitative data suggest that disease progression in these Tg mice is highly dependent on the levels of intracellular Nef proteins.

Tg Expression Evaluated by in situ Hybridization (ISH)

Tg expression was further evaluated by in situ hybridization with $^{35}$S-labeled HIV-1 specific antisense and control sense riboprobes (FIG. 10). The organ and cell type specific pattern of Tg expression detected in the CD4C/HIV$^{Mut}$ Tg mice were very similar to that previously described for the CD4C/HIV$^{wt}$ Tg mice (Hanna, Z et al., J. Virol., 1998, 72:121–132). Briefly, thymic expression of the Tg was most concentrated in the cortical region and to a lesser extent in medullary cells (FIG. 10A), consistent with expression in T cells: in immature CD4+ CD8+ (cortical) and in mature CD4+CD8− (medullary) T cells. In spleen, Tg expression was concentrated in the red pulp and marginal zone of the white pulp. Tg expression was also observed in non-lymphoid tissues. In the kidney, interstitial infiltrating mononuclear cells (FIG. 10E) and cells of unknown identity within glomeruli expressed the Tg. Infiltrating mononuclear cells expressing the Tg were also found in the lamina propria of the intestine (FIG. 11D), in the livers (FIG. 11I) and in the lungs. Liver Kuppfer cells, lung alveolar macrophages (FIG. 10G), peritoneal macrophages (FIG. 10C) and kidney infiltrating macrophages (FIG. 10E) (the latter two identified with α-Mac-1 immunostaining) were positive for Tg expression. However, several other cell types were negative for Tg expression: B-cells, as identified with α-B220 (FIG. 10H), various epithelial cells, smooth muscle and connective tissue cells and epithelial cells of the gastrointestinal tract, renal tubular epithelial cells, pneumocytes, hepatocytes, myocytes of the heart and of skeletal muscle, seminiferous tubules, spermatocytes and vasculature in these organs. Together, these results are consistent with the specificity of the CD4C promoter, as assessed previously (Hanna Z et al., Mol. Cell. Biol., 1994, 14:1084–1094; Hanna, Z et al., J. Virol., 1998, 72:121–132) for CD4+ T cells and for cells of the macrophage/dendritic lineage.

Pathological Assessment of CD4C/HIV$^{Mut}$ Tg Mice

At necropsy, the macroscopic examination revealed severe wasting, edema and atrophy of all lymphoid organs (thymus, spleen and lymph nodes) in a high proportion of the CD4C/HIV$^{MutA}$ and CD4C/HIV$^{MutG}$ diseased Tg mice. These pathological changes were similar to and indistinguishable from those observed previously in CD4C/HIV$^{wt}$ Tg mice (Hanna, Z et al., J. Virol., 1998, 72:121–132). Control non-Tg littermates and CD4C/HIV$^{MutH}$ mice did not exhibit these abnormalities.

The histological examination also revealed changes similar to and indistinguishable from those observed previously in CD4C/HIV$^{wt}$ Tg mice and in the same organs (Hanna, Z et al., J. Virol., 1998, 72:121–132) and present at high frequency in medium- and high-expressor Tg mice. Briefly, these diseased mice exhibited (i) severe depletion of the thymocytes and peripheral lymphocytes accompanied by loss of architecture of the lymphoid organs and fibrosis (FIG. 5B); in some lymph nodes, there was a virtually complete burn out of the T-cell zone, leaving only cortical follicles (B-cells); (ii) lymphoid interstitial pneumonitis (FIG. 11F); (iii) tubulo-interstitial nephritis (with marked tubular atrophy and dilatation and interstitial mononuclear infiltration) (FIG. 11G). This kidney pathology was more often seen in lines in which the Tg was highly expressed (FIG. 11K).

In addition, novel pathologies were observed in some CD4C/HIV$^{MutA}$ and CD4C/HIV$^{MutG}$ mice in which Tg expression was moderate and which survived longer (>4 mo.). These lesions potentially resulted from a more chronic course of disease. Thus, the lung pathology in some animals progressed to include an often extensive intra-alveolar exudate (FIG. 11F). Livers were found with necrotizing granulomas (FIG. 11H). The extent of these granulomas varied from a few small focal lesions in some animals to numerous and sometimes extensive lesions in other animals. Finally, enlargement of the mucosal lymph nodes of the intestine was seen (FIG. 11C). These were occasionaly associated with an infiltration of the lamina propria with mononuclear cells. Again, such pathological Virol., 1998, 72:121–132). Control non-Tg littermates and CD4C/HIV$^{MutH}$ mice did not exhibit these abnormalities.

The histological examination also revealed changes similar to and indistinguishable from those observed previously in CD4C/HIV$^{wt}$ Tg mice and in the same organs (Hanna, Z et al., J. Virol., 1998, 72:121–132) and present at high frequency in medium- and high-expressor Tg mice. Briefly, these diseased mice exhibited (i) severe depletion of the thymocytes and peripheral lymphocytes accompanied by loss of architecture of the lymphoid organs and fibrosis (FIG. 5B); in some lymph nodes, there was a virtually complete burn out of the T-cell zone, leaving only cortical follicles (B-cells); (ii) lymphoid interstitial pneumonitis (FIG. 11F); (iii) tubulo-interstitial nephritis (with marked tubular atrophy and dilatation and interstitial mononuclear infiltration) (FIG. 11G). This kidney pathology was more often seen in lines in which the Tg was highly expressed (FIG. 11K).

In addition, novel pathologies were observed in some CD4C/HIV$^{MutA}$ and CD4C/HIV$^{MutG}$ mice in which Tg expression was moderate and which survived longer (>4 mo.). These lesions potentially resulted from a more chronic course of disease. Thus, the lung pathology in some animals progressed to include an often extensive intra-alveolar exudate (FIG. 11F). Livers were found with necrotizing granulomas (FIG. 11H). The extent of these granulomas varied from a few small focal lesions in some animals to numerous and sometimes extensive lesions in other animals. Finally, enlargement of the mucosal lymph nodes of the intestine was seen (FIG. 11C) . These were occasionaly associated with an infiltration of the lamina propria with mononuclear cells. Again, such pathological changes were not observed in control non-Tg littermates nor in CD4C/HIV$^{MutH}$ Tg mice.

Analysis of Lymphoid Cells from CD4C/HIV$^{Mut}$ Tg Mice

Quantitation of cell numbers in the lymphoid organs of diseased mice showed a severe depletion relative to age-matched controls, especially in Tg mice exhibiting high levels of Tg expression (Table 2).

TABLE 2

Quantitation of cells of lymphoid organs of control and CD4C/HIV$^{Mut}$ Tg mice

| Mouse line (a) | Tg Expression Levels | Number of cells (× 10$^6$) | | |
|---|---|---|---|---|
| | | Thymus | Spleen | Mes. Lymph Nodes |
| Non-Tg (b) | — | 70.9 ± 23 | 61.9 ± 20.8 | 20.3 ± 10.6 |
| CD4C/HIV$^{MutA}$ | | | | |
| F21407 | High | N.D. (c) | 5.2 ± 4.2(*) | 1.1 ± 1.3(*) |
| F21380/21388(d) | Medium | 32.7 ± 30(*) | 33.1 ± 26.5(*) | 9.2 ± 9.3(*) |
| CD4C/HIV$^{MutG}$ | | | | |
| F26990 | High | 7.2(*) | 8.1(*) | 5.4(*) |
| F27367 | Medium | 24.4 ± 1.6(*) | 30.8 ± 15(*) | 5.1 ± 2.4(*) |
| F27372/27011(d) | Medium–Low | 61.7 ± 26.5 | 67.8 ± 24 | 16.4 ± 12.4 |
| CD4C/HIV$^{MutH}$ | | | | |
| F37434 | Medium | 63.8 ± 22.5 | 74.2 ± 24.5 | 32.75 ± 12.7 |

(a) A minimum of five mice of each founder line were used except CD4C/HIV$^{MutG}$ F62990 line where only one animal was analyzed.
(b) The non-Tg control values were obtained by pooling the results of all the non-Tg littermates from different lines.
(c) The thymus of these mice was so atrophied that it could hardly be detected and cells could not be counted.
(d) Results of two founder lines, which express similar protein levels, were pooled.
(*) p < 0.05 by using Student's t-Test.
ND, not determined.

In mice expressing moderate levels of CD4C/HIV$^{MutA}$ and CD4C/HIV$^{MutG}$ Tg and which became diseased later, the total cell number was normal at an early stage and became progessively depleted later. In Tg mice expressing very low levels of these three transgenes and which did not become diseased, the cell number was not statistically different from that of non-Tg controls. Additionally, in mice expressing the CD4/HIV$^{MutH}$ Tg and which did not develop disease, the cell number was not different from control non-Tg mice.

FACS analysis was performed on thymocytes and on cells of the peripheral lymphoid system [blood, spleen and mesenteric lymph nodes (LN)] with antibodies against various cell surface markers for T cells (CD4, CD8, TcRαβ and Thy 1.2) and B cells (B220). For CD4/HIVMutC or CD4/HIVMutH Tg mice which remained in apparent good health, the results of FACS analysis were indistinguishable from those of the control non-Tg littermates (Tables 3 and 4). However, mice from CD4/HIV$^{MutA}$ and CD4/HIV$^{MutG}$ lines all exibited similar abnormal profiles.

TABLE 3

Thymic cells surface marker analysis in CD4C/HIV$^{Mut}$ Tg mice

| Mouse line (a) | Cell populations (%) | | | | Mean Fluorescence (%) (c) | |
|---|---|---|---|---|---|---|
| | Thy 1.2 | CD4$^+$CD8$^+$ | CD4$^+$CD8$^-$ | CD4$^-$CD8$^+$ | Thy 1.2 | CD4 |
| Non-Tg (b) | 91.4 ± 8.4 | 83.2 ± 7.4 | 9.6 ± 3.3 | 4.7 ± 1.7 | 100 | 100 |
| CD4C/HIV$^{MutA}$ | | | | | | |
| F21380/21388 | 91.1 ± 7.2 | 79.6 ± 8.6 | 5.5 ± 1.3(*) | 6 ± 3.9 | 101.6 ± 9.2 | 39.8 ± 24(*) |
| CD4C/HIV$^{MutG}$ | | | | | | |
| F27367 | 93.5 ± 2.1 | 82.3 ± 1.9 | 8.9 ± 0.3 | 9.1 ± 1.1(*)(d) | 94.6 ± 3.5 | 22.3 ± 0.6(*) |
| F27372/27011 | 96.2 ± 1.4 | 87.6 ± 4.7 | 4.8 ± 2.2(*) | 5.4 ± 1.4 | 90.9 ± 11.7 | 35.7 ± 1.8(*) |
| CD4C/HIV$^{MutH}$ | | | | | | |
| F37434 | 95.8 ± 1.3 | 82.7 ± 9.3 | 11.2 ± 2.1 | 4.7 ± 1.2 | 91.7 ± 6.4 | 94.8 ± 11.4 |
| F37435 | 97.1 ± 0.5 | 81.9 ± 0.4 | 11.7 ± 0.6 | 5.76 ± 0.8 | 107.2 ± 5.7 | 97.3 ± 0.6 |

(a) FACS analysis was performed on at least five mice for each mutant line except for CD4C/HIV$^{MutH}$ F37435 line where four animals were analyzed.
(b) The non-Tg control values were obtained by pooling the results of all non-Tg littermates from different lines.
(c) The mean fluorescences for Thy 1.2 and CD4 were obtained by calculating the ratio of CD4 of Thy 1.2 staining in Tg thymuses relative to that of non-Tg thymuses (100%). Mean values were then calculated with the values for each line.
(d) The relative increase of percentage of CD8$^+$ CD4$^-$ cells is likely to reflect the decrease of the CD4 mean fluorescence staining.
(*) $p < 0.05$ by using student's T-Test.

TABLE 4

Mesenteric lymph node cell surface marker analysis in CD4C/HIV$^{Mut}$ Tg mice

| Mouse line (a) | Cell populations (%) | | | | CD4/CD8 Ratio | Mean Fluorescence (%) (d) | |
|---|---|---|---|---|---|---|---|
| | Thy 1.2 | CD4$^+$ | CD8$^+$ | B220 | | Thy 1.2 | CD4 |
| Non-Tg(b) | 63.1 ± 12.4 | 52.5 ± 7.8 | 18.8 ± 4.8 | 21.4 ± 7.1 | 2.94 ± 0.7 | 100 | 100 |
| CD4C/HIV$^{MutA}$ | | | | | | | |
| F21407 | 31.1 ± 0(*) | 24 ± 15.2(*) | 18.7 ± 8.4 | 31.1 ± 18.2(*) | 1.46 ± 0.8(*) | 112.7 ± 14.8 | 45.2 ± 23(*) |
| F21386/21388 | 42.3 ± 7.8(*) | 18.5 ± 6.9(*) | 24.6 ± 7.2(*) | 40.2 ± 9.2(*) | 0.81 ± 0.38(*) | 111.2 ± 8.4 | 24.4 ± 8.8(*) |
| (c) | | | | | | | |
| CD4C/HIV$^{MutG}$ | | | | | | | |
| F26990 | 24(*) | 14.63(*) | 8.4(*) | 68(*) | 1.74(*) | 89.5(*) | 76.8(*) |
| F27367 | 53.5 ± 8(*) | 20.1 ± 6.7(*) | 30.6 ± 4.1(*) | 34.1 ± 7.8(*) | 0.69 ± 0.32(*) | 89.4 ± 1.20 | 13.6 ± 8.7(*) |
| F27372/27011 | 50 ± 4.8(*) | 29.5 ± 4.5(*) | 27.1 ± 5.8(*) | 37.3 ± 5.3(*) | 1.15 ± 0.37(*) | 113.2 ± 18.7(*) | 35.2 ± 11.9(*) |
| (c) | | | | | | | |
| CD4C/HIV$^{MutH}$ | | | | | | | |
| F37434 | 63.4 ± 3.2 | 53.4 ± 6 | 16.9 ± 2 | 25.4 ± 6.5 | 3.2 ± 0.6 | 96.9 ± 11.8 | 96.4 ± 15.5 |
| F37435 | 69 ± 6.5 | 50.8 ± 6.1 | 25.1 ± 2.3 | 21.1 ± 7.8 | 2.03 ± 0.03 | 108.9 ± 16.6 | 104.1 ± 25.2 |

(a) FACS analysis was performed on at least five mice for each Tg line except for CD4C/HIV$^{MutH}$ F37435 line where four animals were used and for CD4C/HIV$^{MutG}$ F26990 where only one mouse was analyzed.
(b) The non-Tg control values were obtained by pooling the results of all non-Tg littermates from different lines.
(c) The results of two founders expressing similar protein levels, except CD4/HIV$^{MutC}$, were pooled.
(d) The mean fluorescences for Thy 1.2 and CD4 were obtained by calculating the ratio of CD4 or Thy 1.2 staining in Tg L.N. relative to that of non-Tg L.N. (100%). Mean values were then calculated with the values for each line.
(*) $p < 0.05$ by using student's T-Test.

In the thymus, a decrease of the CD4 staining (Mean Fluorescence) of the single (CD4+CD8−) and double- (CD4+CD8+) positive cells could be observed at an early stage, even before a loss of cells could be documented (Table 4 and FIG. 12A). As the disease progressed and in cell-depleted thymuses, the CD4 mean fluorescence continued to decrease until becoming undetectable. The percentage of CD4+CD8+ and Thy1.2+ populations were not significantly different from those of non-Tg littermates, even in thymuses with significant cell loss. However, in the medium- and high-expressor Tg mice, a decrease of the CD4+CD8− and of the TcRhigh positive T cells, which represent the mature T cells, could be observed (Table 3, FIG. 12A).

The same analysis performed on peripheral lymphoid cells [spleen, blood, mesenteric LN (Table 4 and FIG. 12B)] also showed that CD4/HIV$^{MutA}$ and CD4/HIV$^{MutG}$ Tg mice all exibit similar abnormalities. A progressive decrease of the CD4 (but not of the Thy1.2) cell surface mean fluorescence was sometimes reflected by the appearance of CD4Low and CD4High cells (see FIG. 12B, F27011; mean fluorescence, Table 4). In addition, at an early stage, in medium- or high-expressor mice, a depletion of Thy1.2+ T cells and more specifically of the CD4+ T cells, often accompanied by an increase of CD8+ T cells, could also be observed.

This increase of the CD8+ T cells was best seen in mesenteric LN of medium-expressor mice and was less often observed in the spleen. The CD4/CD8 ratio was significantly decreased in these mice (Table 4). At a later stage, particularly in medium- or high-expressor mice, the numbers of both CD4+ and CD8+ T cells were dramatically reduced. The proportion of B220+ B-cells in the peripheral organs was found to be increased in these three mutant mice relative to their control non-Tg littermates, possibly reflecting the T-cell depletion in these organs.

The lymphoproliferative capacity of the lymphoid cells of CD4C/HIV$^{MutG}$ (F27367) Tg mice was also assessed before they showed signs of clinical disease. Anti-CD3 stimulated total spleen and mesenteric LN cells from these mice showed a decrease 3H-thymidine incorporation at only 25.6±15.4% (n=4) and 35.8±25.1% (n=4) of the control non-Tg littermates, respectively indicating functional defects of T-cells in these mice. The same spleen and LN cells stimulated with LPS proliferated at 110±33% (n=4) and 170±132% (n=4) of the control, respectively, suggesting some hyperresponsiveness of the B-cells in these mice.

HIV-1 Nef Harbors the Major Determinant of Pathogenicity in Tg Mice

In an effort to identify the viral gene(s) responsible for the development of a severe AIDS-like disease in Tg mice expressing the complete HIV-1 genome in CD4+ T cells and in cells of the monocyte/macrophage lineage, we constructed 5 distinct HIV-1 mutant genomes which were assayed in 18 lines of Tg mice. This mutational analysis revealed that this AIDS-like phenotype could be induced by the expression of a single HIV-1 gene, nef and that the other HIV-1 genes were dispensable for the emergence of this phenotype. This result was rather surprising in view of the fact that other HIV-1 proteins had previously been reported to have profound effects on host cell functions in vitro or in vivo. In vitro studies had indeed showed that Vpr was able to induce terminal differentiation of rhabdosarcoma cells and was cytostatic for T-cells, arresting them in G2. Vpu is known to induce degradation of the CD4 protein. Tat has been reported to inhibit antigen-induced proliferation of T-cells and to induce apoptosis of T-cells. The envelope gp120 and gp41 glycoproteins have been shown to induce cell fusion and apoptosis and to affect T-cell signaling. However, the vpr, vpu, tat and env genes were dispensable for the development of the disease in CD4C/HIV$^{Mut}$ Tg mice. The dispensable role of env gp120 in the development of the disease in CD4C/HIVMut Tg mice may be related to the absence of its proper receptor (the human CD4 protein) or its co-receptors in these mice. Experiments are in progress to determine whether the concomitant expression of these receptors will unmask a function of the envelope glycoproteins in these Tg mice.

In vivo effects of some HIV-1 genes in the absence of virus replication have been best studied in Tg mice. Impressive phenotypes, such as cataracts, epidermal hyperplastic growth and a severe nephropathy were induced (Klotman P E et al., AIDS, 1995, 9:313–324). However, none of the HIV-1 genes, except nef, when expressed in CD4+ immune cells of CD4C/HIVMut Tg mice led to an observable phenotype and apparently contributed to the development of the severe AIDS-like disease, thus suggesting that the cell type in which some HIV-1 proteins are expressed is a major factor in determining their effect.

In more related studies, HIV-1 nef was expressed in T-cells of Tg mice using the promoter/enhancer elements of the CD3δ (Skowronski, J et al., Embo J., 1993, 12:703–713), CD2 (Brady, H. J. et al., EMBO J., 1993, 12:4923–4932) or T-cell receptor (TcR) β (chain (Lindemann D et al., J. of Experimental Medicine, 1994, 179:797–807) gene. In some of these Tg mice, a severe immunodeficiency with loss of T-cells and alterations of T-cell activation was observed. However, none of these nef Tg mice developed a multiorgan syndrome and an immune disease similar to the one observed in CD4C/HIV$^{MutG}$ Tg mice of the present invention and which most closely mimics the human AIDS. The different phenotypes observed in these nef expressing Tg mice and in the CD4C/HIV$^{MutG}$ Tg mice studied here, is likely to reflect the cell type(s) expressing the Tg. In contrast to these Tg mice in which the Tg was expressed in several subsets of T-cells, expression of nef in CD4C/HIV$^{MutG}$ Tg mice was not only in the CD4+ T-cell subset but also in cells of the monocyte/macrophage lineage, the same cells as those found infected in HIV-1 positive individuals. Thus, the specific cell subsets expressing nef in CD4C/HIV$^{Mut}$ Tg mice may have been critical for inducing this AIDS-like disease. The differences in the levels of Tg expression in CD4C/HIV$^{Mut}$ Tg mice and in those nef-expressing Tg mice are unlikely to explain the different phenotypes observed, since the same AIDS-like disease developed, but after longer latent periods, in CD4C/HIV$^{Mut}$ Tg mice expressing the Tg at lower levels.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A transgenic or chimeric mouse to serve as a small animal model of AIDS wherein at least the somatic cells of said mouse comprises a transgene comprising a DNA sequence encoding HIV-1 in operable linkage with the human CD4 promoter flanked by the enhancer of the mouse CD4 gene, wherein said transgene is expressed in T-cells and in cells of monocyte/macrophage lineage, and wherein expression of said transgene is sufficient to effect phenotypic changes consistent with AIDS pathology.

2. A transgenic mouse to serve as a small animal model of AIDS in which at least the somatic cells comprise a transgene that comprises:
   a) a HIV-1 coding sequence; and
   b) a human CD4 gene promoter operatively linked to said HIV-1 coding sequence, wherein said promoter is flanked by the enhancer of the mouse CD4 gene for expression in T-cells and in cells of monocyte/macrophage lineage, and wherein said transgene is introduced into said mouse or an ancestor thereof as a single transgene, and wherein expression of said transgene is sufficient to effect phenotypic changes consistent with AIDS pathology.

3. The transgenic mouse of claim 1, wherein said human CD4 gene promoter is linked at the 3' end of said HIV-1 DNA genome.

4. The transgenic mouse of claim 2, wherein said human CD4 gene promoter is linked at the 3' end of said HIV-1 DNA genome.

5. A method for producing a transgenic mouse to serve as a small animal model of AIDS, which comprises the steps of:

a) transferring a transgene into a mouse fertilized oocyte, wherein the transgene comprises:
   i) a HIV-1 coding sequence; and
   ii) a human CD4 gene promoter operatively linked to said HIV-1 coding sequence, wherein said promoters flanked by the enhancer of the mouse CD4 gene for expression in T-cells and in cells of monocyte/macrophage lineage;

b) transferring a fertilized oocyte containing the transgene to the uterus of a female mouse;

c) maintaining the mouse of step b) such that said mouse becomes pregnant with an embryo derived from said fertilized oocyte, and allowing said embryo to develop to term; and d) selecting a transgenic mouse whose genome comprises said transgene;

wherein expression of said transgene is sufficient to effect phenotypic changes consistent with AIDS pathology.

6. A chimeric mouse to serve as a small animal model of AIDS in which at least the somatic cells comprise a transgene that comprises:
   a) a HIV-1 coding sequence; and
   b) a human CD4 gene promoter operatively linked to said HIV-1 coding sequence, wherein said promoter is flanked by the enhancer of the mouse CD4 gene for expression in T-cells and in cells of monocyte/macrophage lineage, and wherein said transgene is introduced into said mouse or an ancestor thereof as a single transgene, and wherein expression of said transgene is sufficient to effect phenotypic changes consistent with AIDS pathology.

7. A method for producing a chimeric mouse to serve as a small animal model of AIDS, which comprises the steps of:
   a) transferring a transgene into a mouse embryonic stem cell line, wherein the transgene comprises:
      i) a HIV-1 coding sequence; and
      ii) a human CD4 gene promoter operatively linked to said HIV-1 coding sequence, wherein said promoter is flanked by the enhancer of the mouse CD4 gene for expression in T-cells and in cells of monocyte/macrophage lineage;

b) selecting an embryonic stem cell line whose genome comprises said transgene;

c) introducing the embryonic stem cell line of step b) into a viable blastocyst;

d) transferring the injected blastocyst having the embryonic cells into a pseudopregnant female mouse;

e) screening for a chimeric mouse born to the female mouse which include the transgene;

wherein expression of said transgene in said chimeric is sufficient to effect phenotypic changes consistent with AIDS pathology.

8. The mouse of claim 1 wherein the phenotypic change is wasting.

9. The mouse of claim 1 wherein the phenotypic change is atrophic lymphoid organs.

10. The mouse of claim 1 wherein the phenotypic change is atrophic kidneys.

11. The mouse of claim 1 wherein the phenotypic change is a thickening of alveolar walls by infiltrating cells of lymphoid morphology.

12. The mouse of claim 1 wherein the phenotypic change is early death.

13. The mouse of claim 1 wherein the phenotypic change is elevated expression of RANTES in various tissues.

14. A method to screen for potential therapeutic agents for the treatment of AIDS, which comprises the steps of:
   a) administering the potential therapeutic agent to the mouse of claim 1; and
   b) determining the effects of the potential therapeutic agent on the AIDS pathology of said mouse.

15. A method to screen for potential therapeutic agents for the treatment of AIDS, which comprises the steps of:
   a) administering the potential therapeutic agent to the mouse of claim 2; and
   b) determining the effects of the potential therapeutic agent on the AIDS pathology of said mouse.

* * * * *